(12) United States Patent
Khair

(10) Patent No.: US 8,838,218 B2
(45) Date of Patent: Sep. 16, 2014

(54) LEADLESS WIRELESS ECG MEASUREMENT SYSTEM FOR MEASURING OF BIO-POTENTIAL ELECTRICAL ACTIVITY OF THE HEART

(76) Inventor: Mohammad Khair, Irvine, CA (US)

(*) Notice: Subject to any disclaimer, the term of this patent is extended or adjusted under 35 U.S.C. 154(b) by 197 days.

(21) Appl. No.: 13/191,080

(22) Filed: Jul. 26, 2011

(65) Prior Publication Data

US 2012/0165633 A1   Jun. 28, 2012

Related U.S. Application Data

(60) Provisional application No. 61/460,233, filed on Dec. 28, 2010, provisional application No. 61/460,254, filed on Dec. 28, 2010.

(51) Int. Cl.
*A61B 5/0402* (2006.01)
*A61B 5/0408* (2006.01)
*A61B 5/00* (2006.01)

(52) U.S. Cl.
CPC ......... *A61B 5/04085* (2013.01); *A61B 5/04028* (2013.01); *A61B 5/6833* (2013.01)
USPC ...................................................... 600/509

(58) Field of Classification Search
None
See application file for complete search history.

(56) References Cited

U.S. PATENT DOCUMENTS

| 7,485,095 B2* | 2/2009 | Shusterman | 600/508 |
| 7,647,093 B2* | 1/2010 | Bojovic et al. | 600/509 |
| 7,827,011 B2* | 11/2010 | DeVaul et al. | 702/190 |
| 8,150,502 B2* | 4/2012 | Kumar et al. | 600/509 |
| 8,315,695 B2* | 11/2012 | Sebelius et al. | 600/509 |
| 2010/0234746 A1* | 9/2010 | Sebelius | 600/509 |

* cited by examiner

*Primary Examiner* — Kennedy Schaetzle
(74) *Attorney, Agent, or Firm* — Davis Chin; Davis M. Chin, Jr.

(57) ABSTRACT

A leadless wireless ECG measurement system for measuring of bio-potential electrical activity of the heart in a patient's body includes at least one multi-contact bio-potential electrode assembly adapted for attachment to the patient's body. The electrode assembly is formed of an electronic patch layer and a disposable electrode layer. The disposable electrode layer has a plurality of contact points for engagement with the surface of the patient's body and is configured to measure short-lead ECG signals in response to electrical activity in the heart. A processing unit is provided and is configured to produce a transfer function which computes estimated long-lead ECG signals based on the measured short-lead ECG signals from the plurality of contact points.

27 Claims, 15 Drawing Sheets

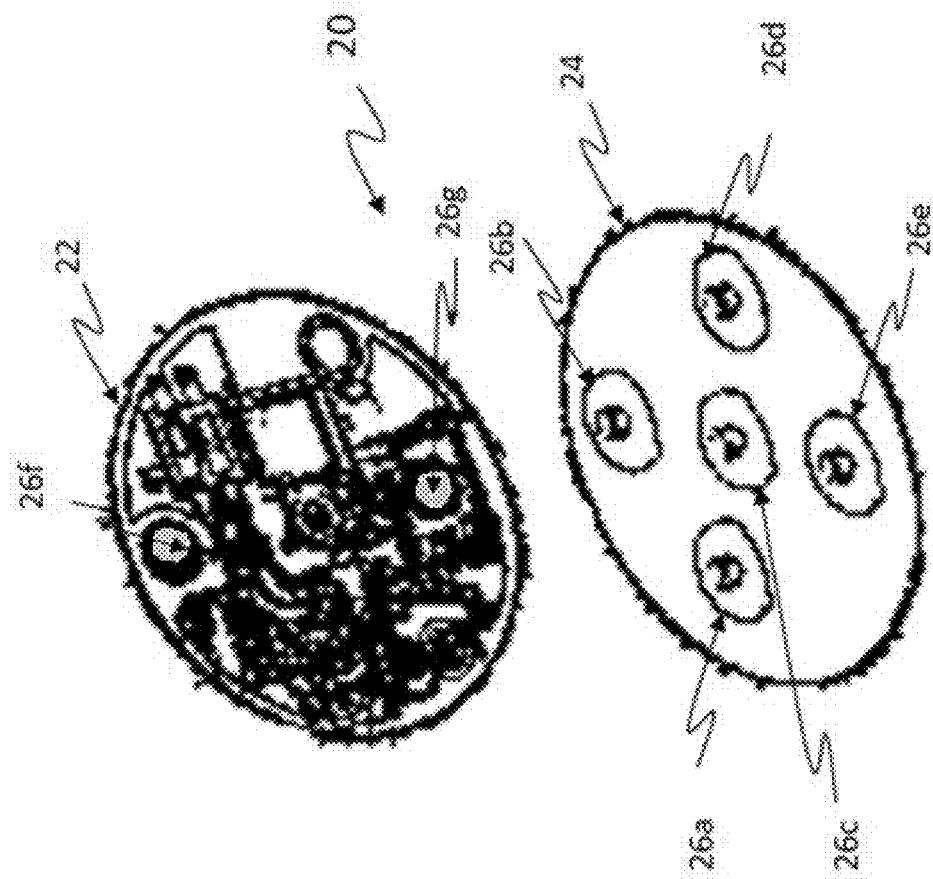

Fig. 9 (a)-(d)

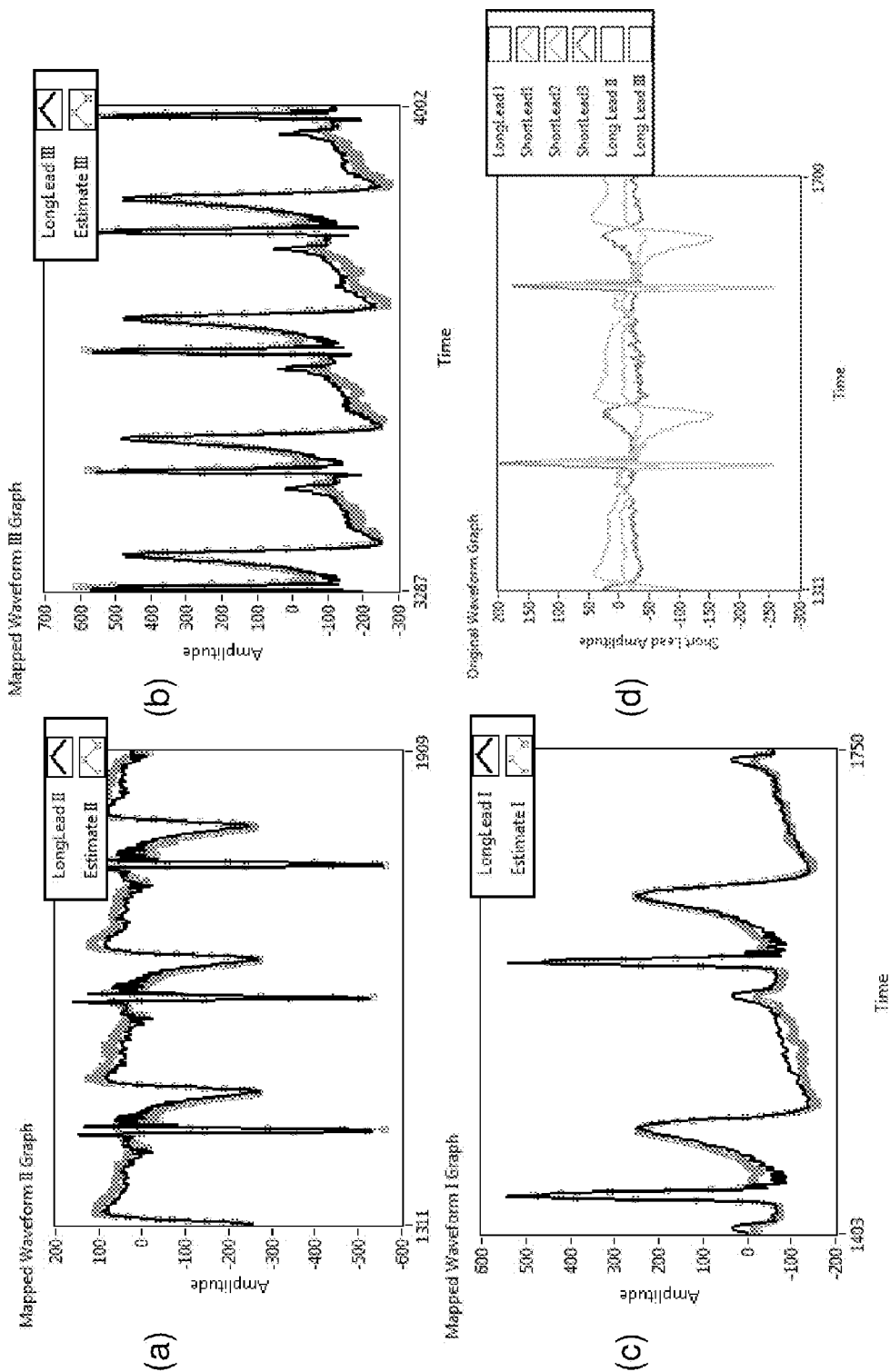
Fig.11 (a)-(d)

LEADLESS WIRELESS ECG MEASUREMENT SYSTEM FOR MEASURING OF BIO-POTENTIAL ELECTRICAL ACTIVITY OF THE HEART

CROSS-REFERENCE TO RELATED APPLICATIONS

This application is a non-provisional application which claims the benefits of provisional application Ser. No. 61/460,233 filed on Dec. 28, 2010 and Ser. No. 61/460,254 filed on Dec. 28, 2010.

BACKGROUND OF THE INVENTION

1. Technical Field

This invention relates generally to wireless ECG bio-potential measurement devices for measuring electrical bio-potential signals generated by the heart. More particularly, it relates to a new and improved leadless wireless ECG measurement system and method for measuring of bio-potential electrical activity of the heart that uses measurements obtained across a much smaller separation distance between electrode contact points, but yet retains the presentation of ECG waveforms which corresponds closely to existing ECG measurement standards, thereby preserving the waveform morphology, amplitude, and frequency components.

2. Prior Art

As is generally known in the art, an electrocardiograph is widely used by the medical profession in order to obtain an ECG (electrocardiogram) which is a measurement of bio-potential electrical activity of the heart from the surface of the skin. The conventional 12-lead electrocardiograph typically requires at least 10 wires to be attached via electrodes to the body of the patient at one end and to the electrocardiograph at the other end so as to measure the bio-potentials representing heart-signals and to transfer them via bipolar and unipolar leads into a 12-lead electrocardiogram.

ECG measurements have been conducted for over 200 years, and a standard configuration of the measurement vector leads have been adopted by the medical and engineering communities. This standard of leads formation and configuration require substantial separation of points of measurements on the surface of the skin, which necessitates connection of two remote points by lead wires into an instrumentation amplifier. This large separation between electrode contact points maximizes the surface area of the skin between the measurement electrode points and therefore maximizes the impedance, and measured voltage potential across the contact electrodes.

In early years, this was necessary for measurement of ECG due to lack of electronics that satisfy the measurement quality, signal-to-noise ratio, and cost constraints. Today, however, current electronics resolution, noise rejection, and amplification strength allows for ECG measurements across a much smaller separation distance between the contacting electrodes. ECG measurement standards, however, have been largely set and adopted with the original configuration of contact points preserving large separation distances between contacting electrodes.

The instrumentation amplifier is ideally used for the measurement of the ECG. The instrumentation amplifier typically rejects common mode noise using a common reference electrode to its two bipolar inputs, and amplifies the difference in potential between the two measurement electrodes as the measured bio-potential value. This bio-potential changes dynamically with the cardiac contraction and dilation due to depolarization and re-polarization of the cardiac muscle. The electric activity emanates from the Sinoatrial node (SA node) and spreads through the Purkinji fibers from the atrial upper portion to the ventricular portion of the cardiac muscle.

The electric activity surfaces from the cardiac muscle to the skin and dissipates throughout the conductive skin layer. Since the skin has electric impedances, the conductivity of the electric current varies depending on the direction of the measurement and the separation distance of between the measurement electrodes. The skin impedance varies dynamically depending on multiple factors, including the hydration status of the skin, blood flow vasodilators or vasoconstrictors, medications, cardiac output to name a few.

It will be noted that the 12-lead ECG provides spatial information about the heart's electrical activity in 3 approximately orthogonal directions. The orthogonal directions are namely (1) Right to Left, (2) Superior to Inferior, and (3) Anterior to Posterior. Thus, the standard ECG measurement involves the attachment of six electrodes to the chest or precordial area of the patient to obtain recordings of leads V1 through V6 and the attachment of four electrodes to the arms and legs in order to obtain recordings of leads I, II, III, AVR, AVL, and AVF. Subsequent to the attachment of the ten electrodes to the patient, there is then required the connecting of ten specific wires between each particular electrocardiograph terminal and the related electrodes of predetermined position.

In U.S. Pat. Nos. 6,441,747 to Khair et al. and 6,496,705 to Ng et al., there are disclosed a wireless, programmable system for bio-potential signal acquisition which includes a base unit and a plurality of individual wireless, remotely programmable transceivers connected to patch electrodes. The base unit manages the transceivers by issuing registration, configuration, data acquisition, and transmission commands using wireless techniques. The bio-potential signals from the wireless transceivers are demultiplexed and supplied via a standard interface to a conventional ECG monitor for display.

Further, there is shown in U.S. Pat. No. 7,403,808 to Istvan et al. a cardiac monitoring system for detecting electrical signals from a patient's heart and wirelessly transmit the signals digitally to a remote base station via telemetry. The base station converts the digital signals to analog signals which can be read by an ECG monitor.

In U.S. Pat. No. 5,862,803 to Besson et al., there is described a wireless medical diagnosis and monitoring equipment which includes an evaluation station and a plurality of electrodes which are arranged on a patient. Each of the plurality of electrodes includes elementary sensors, sensor control, transceivers, and transmission control units which are integrated in one single semiconductor chip.

In U.S. Pat. No. 4,981,141 to Jacob Segalowitz, there is disclosed an electrocardiographic monitoring system in which the heart-signal sensing electrodes are each coupled to the heart-signal monitor/recorder by respective wireless transmitters and corresponding respective receiving wireless receivers in a base unit.

One of the disadvantages encountered in the operation of the conventional ECG devices is that they utilize a large separation between the electrode contact points which requires maximum surface area of the skin and thus maximizes impedance and measured voltage potential across the contact electrodes. Another disadvantage suffered by the prior art ECG devices is that the numerous lengthy terminal wires coupled to the electrodes will frequently obstruct the patient and limit the freedom of movement of the patient. Further, the terminal wires often become intertangled with one another during their use, thereby rendering them difficult and cumbersome for the physician and/or technician. In addition, the conventional ECG devices and their attaching electrodes suffer from the problem of having a relatively large footprint.

Therefore, it would be desirable to provide a leadless wireless ECG measurement system and method for measuring of bio-potential electrical activity of the heart which operates on a more efficient and effective basis. Further, it would be expedient that the ECG measurement system overcomes all of the afore-mentioned shortcomings of the prior art discussed in connection with the application of the conventional electro-cardiographs used to obtain the electrocardiogram. The present invention represents a significant improvement over the aforementioned prior art U.S. Pat. Nos. 6,441,747; 6,696,705; 7,403,808; 5,862,803; and 4,981,141 which are hereby incorporated by reference in their entirety.

BRIEF SUMMARY OF THE INVENTION

The wireless ECG measurement system of the present invention performs measurements of ECG in a leadless configuration using a minimal number of bio-potential measurements across a short distance (approximately 1 to 3 inches and referred to as "short-leads") which represent input waveforms to a model, and then maps these ECG measurements using a plurality of identified mathematical models (or functions) to the standard 12-lead configuration representing the model outputs. The final output is presented to the end user as an estimated calculated ECG of up to 12 standard ECG leads. The short lead measurements do not require extended lead wires due to the proximity of distance between the measurement points, and the measurement electrode contact points can be integrated in a single electrode patch that has a plurality of contact points with the surface of the skin for conducting the measurements.

In view of the foregoing background, it is therefore an object of the present invention to provide a leadless wireless ECG measurement system and method for measuring of bio-potential electrical activity of the heart of improved design and performance. It is another object of the present invention to provide a leadless wireless ECG measurement system and method for measuring of bio-potential electrical activity of the heart which uses measurements across a much smaller separation distance between the electrode contact points. It is still another object of the present invention to provide an ECG measurement system and method which is much more compact in its form and coverage area between the contacting points on the surface of the skin. It is still yet another object of the present invention to provide an ECG measurement system and method which produces a higher degree of comfort for the patient by eliminating lead wires extending to distal electrodes, is easier to use and has more flexibility of placement for the clinician without a tradeoff of accuracy, and has a smaller footprint than the conventional ECG devices.

These and other objects, features and advantages of the invention are provided by a leadless wireless ECG measurement system for measuring of bio-potential electrical activity of the heart in a patient's body which includes at least one multi-contact bio-potential electrode assembly adapted for attachment to the patient's body. The electrode assembly is formed of an electronic patch layer and a disposable electrode layer. The disposable electrode layer has a plurality of contact points for engagement with the surface of the patient's body and is configured to measure short-lead ECG signals in response to electrical activity in the heart.

Advantageously, the electronic patch layer of the present invention further has a transceiver unit for transmitting and receiving wireless communications with a base station or with other patch electrode assemblies.

Further, a processing unit is provided and is configured to produce a transfer function which computes standard long-lead ECG signals based on the measured short-lead ECG signals from the plurality of contact points. The base station includes a wireless transceiver for transmitting and receiving communications with the plurality of contact points in the disposable electrode layer. The wireless communications received by the wireless transceiver includes the standard long-lead ECG signals.

In addition, a monitor is coupled to receive the long-lead ECG signals from the base station for displaying meaningful information.

These and other features and advantages of the disclosed leadless wireless ECG measurement system reside in the construction of parts and the combination thereof, the mode of operation and use, as will become more apparent from the following description, reference being made to the accompanying drawings that form a part of this specification wherein like reference characters designate corresponding parts in the several views. The embodiments and features thereof are described and illustrated in conjunction with systems, tools and methods which are meant to exemplify and to illustrate, not being limiting in scope.

BRIEF DESCRIPTION OF THE SEVERAL VIEWS OF THE DRAWING

FIG. 2 is an enlarged, perspective view of the multi-contact bio-potential electrode assembly of FIG. 1, with the electronic patch layer being illustrated separate and apart from the disposable electrode layer;

FIGS. 11(a) through 11(d) are sample plots depicting estimated long standard leads I, II, and III from measured short leads at locations RA, LA, and LL.

DETAILED DESCRIPTION OF THE INVENTION

Figure 1:
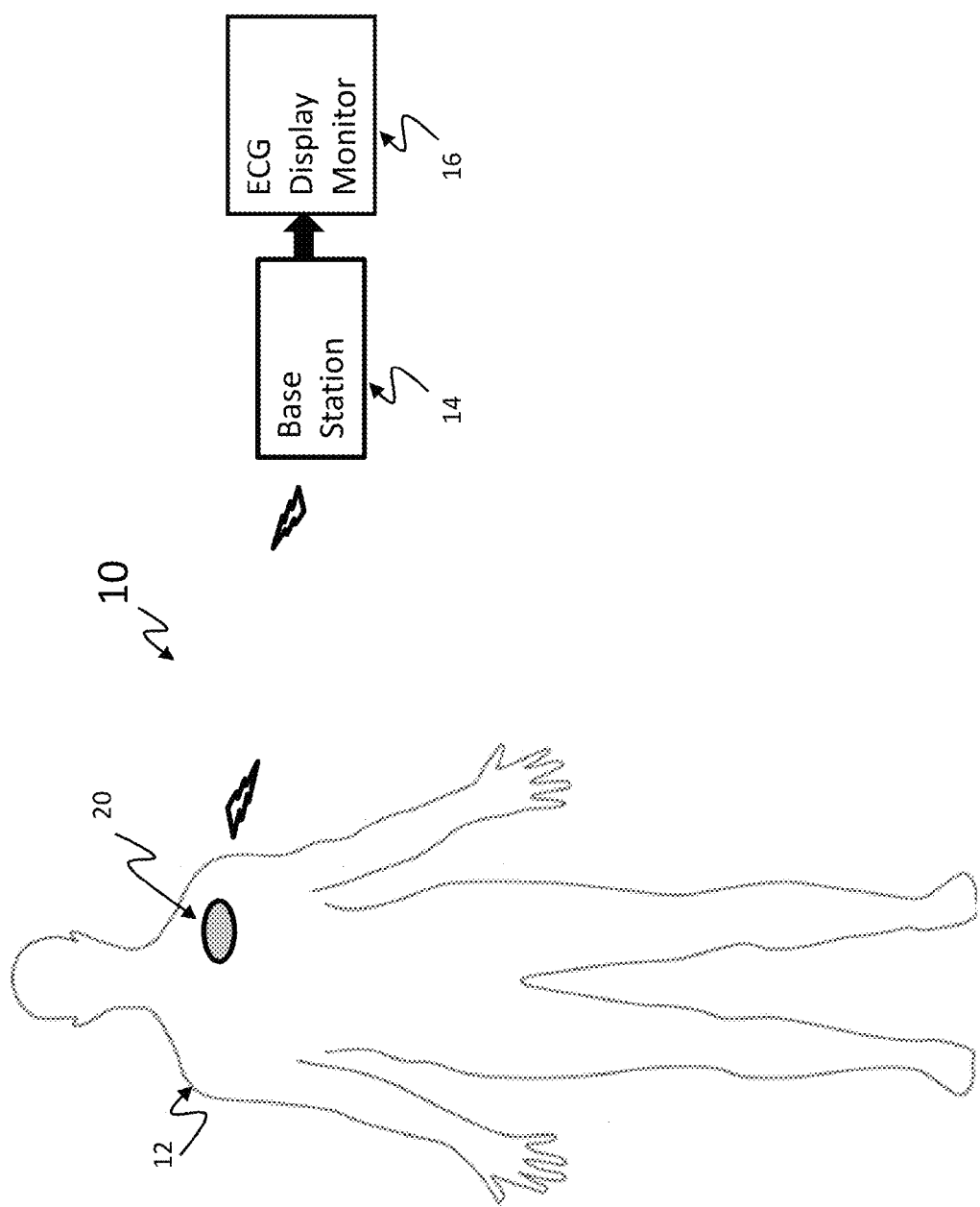
FIG. 1 is a schematic representation of a wireless ECG measurement system for use with a patient so as to acquire ECG signals via "short leads" and to deliver them to an ECG monitor, constructed in accordance with the principles of the present invention.
Figure 1C:
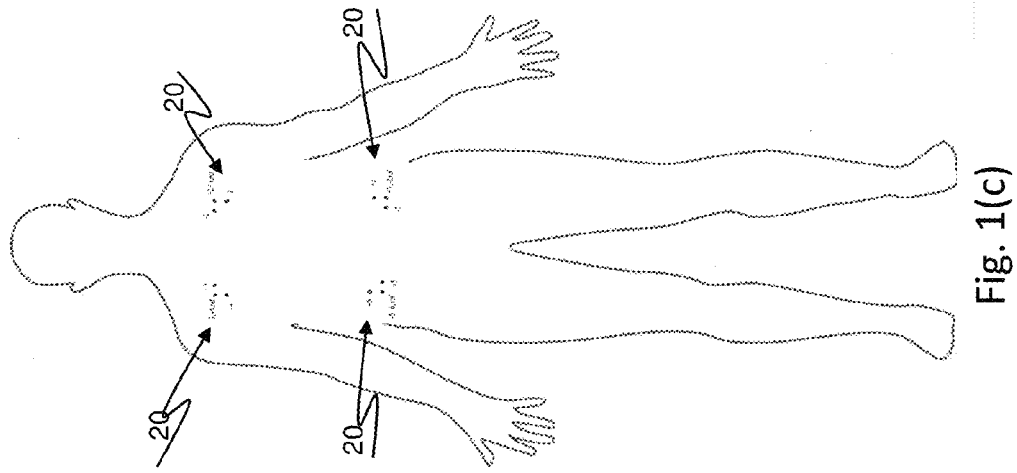
FIGS. 1(a) through 1(f) depict the various preferred locations that a plurality of electrode assemblies of the present invention may be placed on a patient's body.

Before explaining the disclosed embodiments in detail, it is to be distinctly understood at the outset that the present invention shown in the drawings and described in detail in association with a leadless wireless ECG system for measuring of bio-potential electrical activity of the heart is not intended to serve as a limitation upon the scope or teachings thereof, but is to be considered merely for the purpose of convenience of illustration of one example of its application.

Referring now in detail to the various views of the drawings, there is illustrated in FIG. 1 a leadless wireless ECG measurement system for measuring of bio-potential electrical activity of the heart in a patient's body, which is designated generally by reference numeral 10 and is constructed in accordance with the principles of the present invention. The ECG measurement system 10 acquires "short-lead" ECG heart-signals from the body 12 of the patient and transmits them wirelessly to a receiving base station or unit 14. The receiving base station 14 transmits the heart-signals to an ECG monitor 16 for displaying meaningful information to a physician or technician.

Figure 1B:
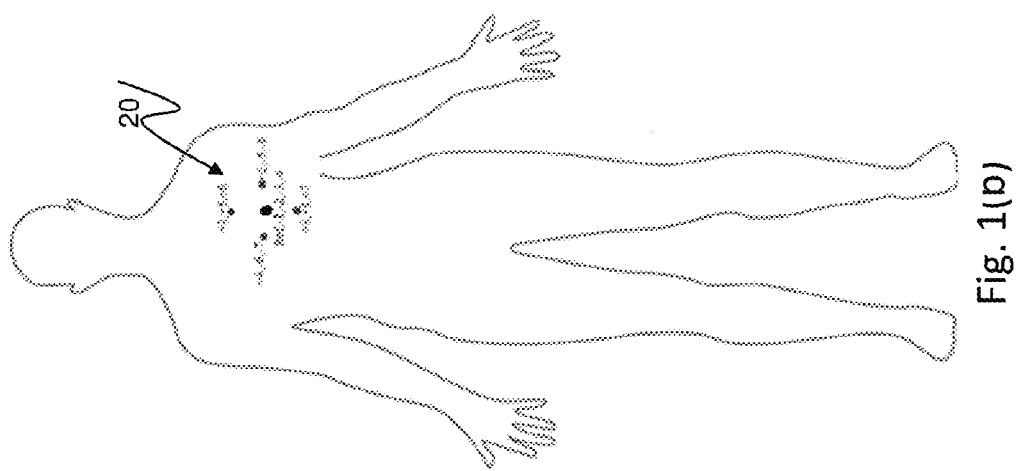
Figure 1A:
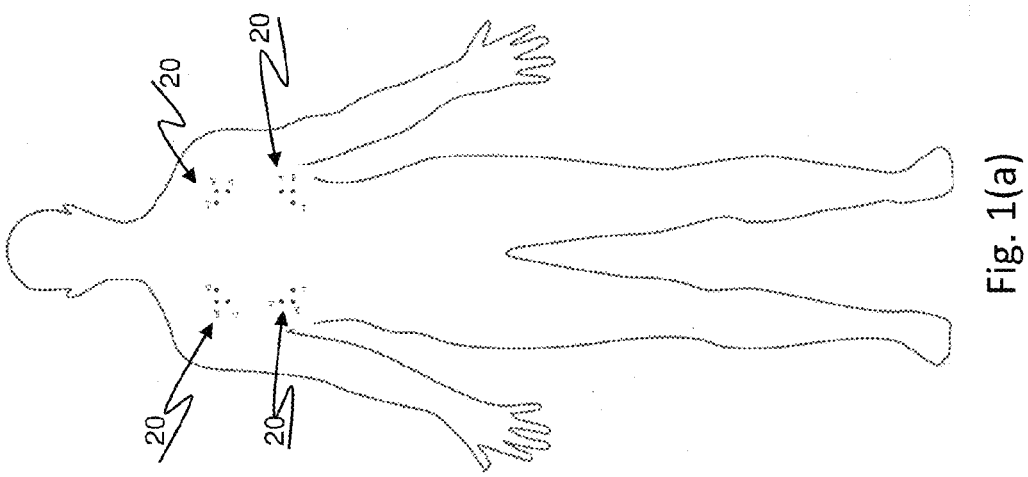
Figure 1F:
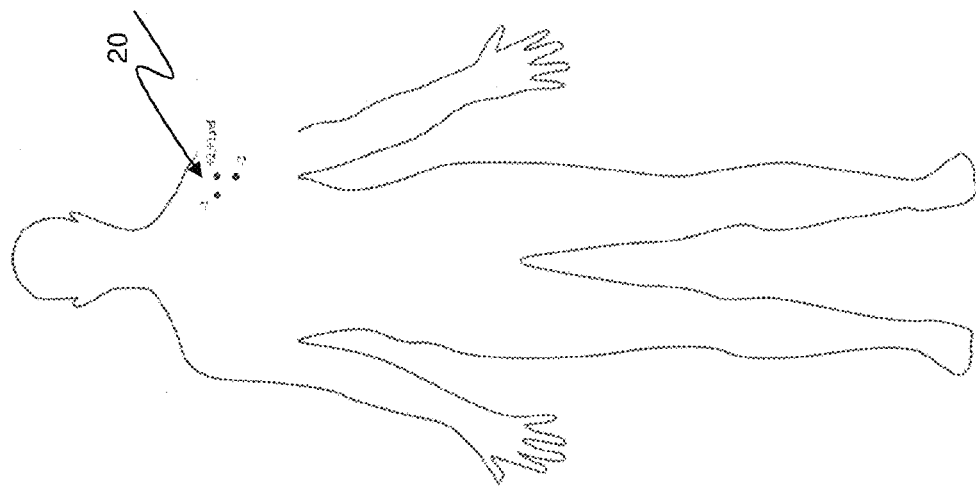
Figure 1E:
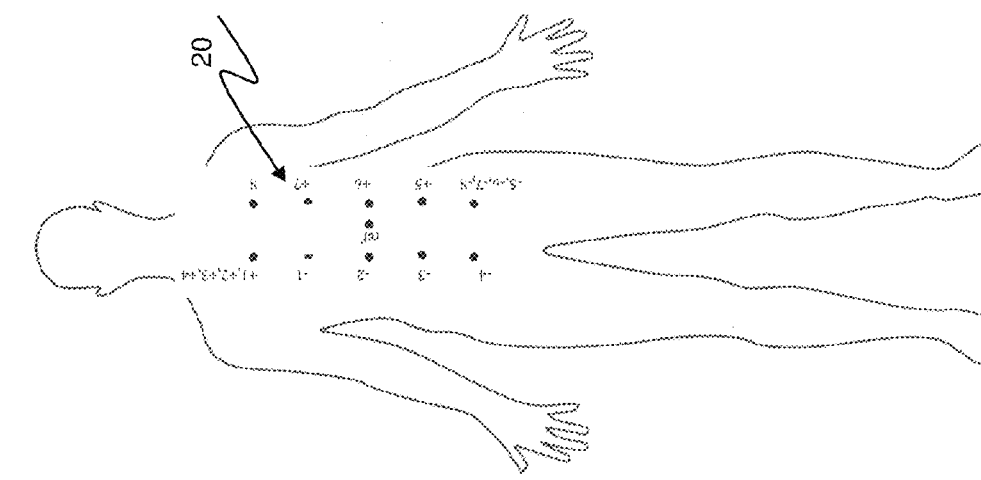
Figure 1D:
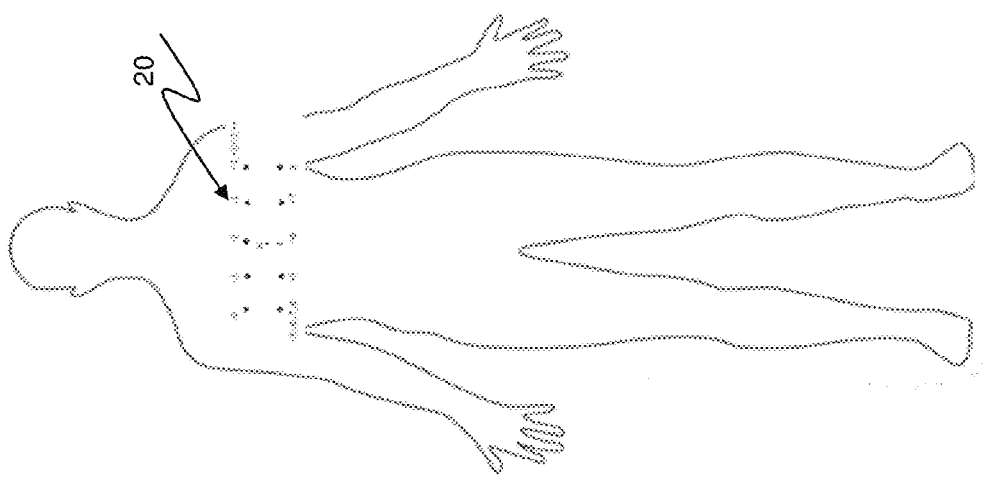
Figure 1G:
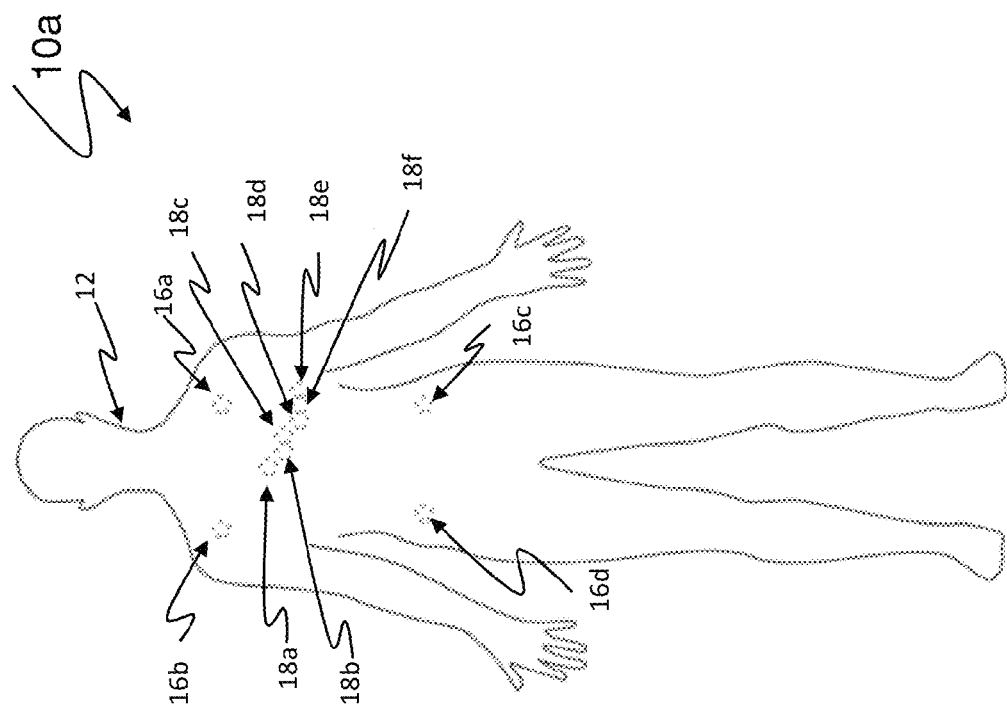
FIG. 1(g) depicts the electrodes 16a-16d and the electrodes 18a-18f disposed on the patient's body to obtain the respective limb lead signals and precordial lead signals in the standard ECG measurement system.
Figures 2A, 2B, 2C, 2D, 2E, 2F, 2G:
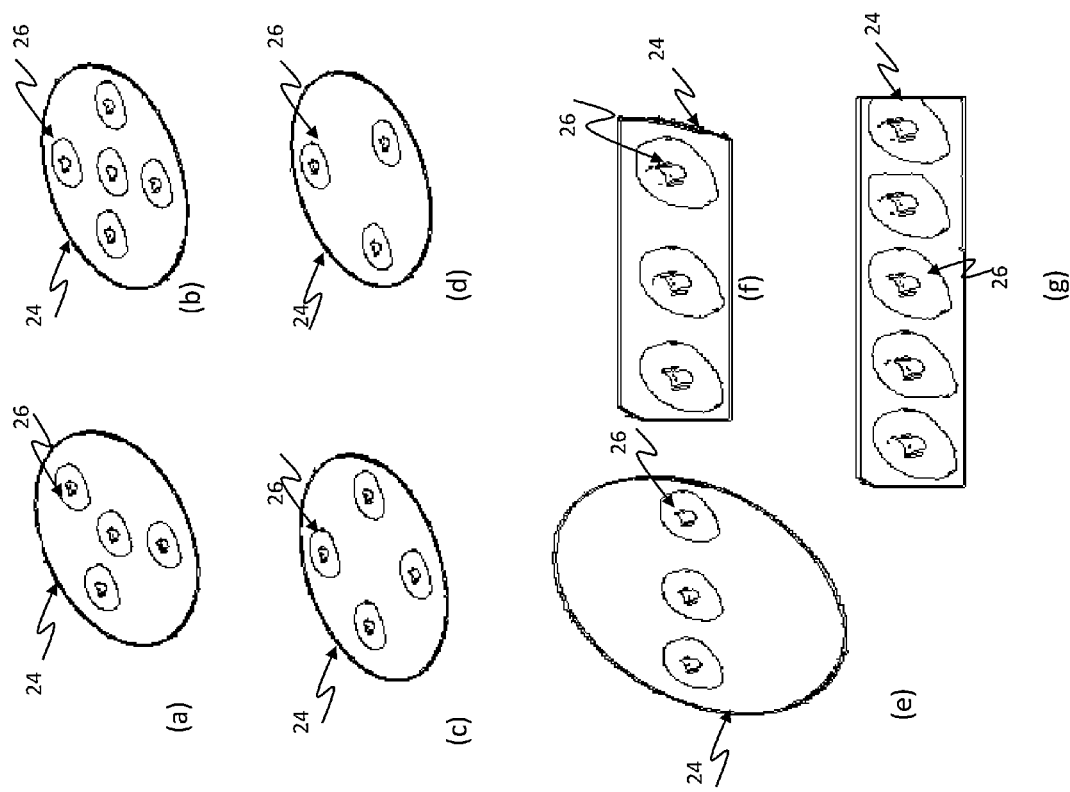
FIGS. 2(a) through 2(g) depict various configurations of the disposable electrode layer each having a plurality of contact points arranged on its surface.

As shown in FIG. 1(g), the standard ECG measurement system 10a includes a plurality of electrodes or contact points 16a, 16b and 16c disposed on the patient's body in order to obtain limb lead signals I, II, and III. The electrode or contact point 16a is attached to the patient's left arm or shoulder (LA). The electrode 16b is attached to the patient's right arm or shoulder (RA). The electrode 16c is attached to the patient's left leg or lower left abdomen (LL). The electrode 16d is attached to the patient's right leg or lower right abdomen (RL). In addition, there is illustrated in FIG. 1(g) a plurality of electrodes or contact points 18a, 18b, 18c, 18d, 18e and 18f which are attached to the chest or precordial area so as to obtain the precordial lead signals V1, V2, V3, V4, V5 and V6. In summary, the standard 12-lead ECG system is defined by the following:

Lead I between LA and RA
Lead II between RA and LL
Lead III between LA and LL
Calculated augmented leads aVF, aVR, and aVL
V1: right 4th intercostal space
V2: left 4th intercostal space
V3: halfway between V2 and V4
V4: left 5th intercostal space, mid-clavicular line
V5: horizontal to V4, anterior axillary line
V6: horizontal to V5, mid-axillary line Further, the ECG measurement system 10 of the present invention includes at least one multi-contact bio-potential electrode assembly 20 also disposed on the patient's body 12 which is comprised of an electronic patch layer 22 and a disposable electrode layer 24 to which the patch layer 22 is attached on top thereof. As can be best seen in FIG. 2, the electrode layer 24 includes a plurality (five) of contact or sensor points defining contacts 26a through 26e for engagement with the surface of the patient's skin for conducting the measurements. While the electrode layer 24 depicted with five contacts, it should be clearly understood by those skilled in the art that any number of contacts, more or less, may be used alternately as desired. However, it is preferable that three, four, or five contacts be utilized.

For reference, the ECG waveforms measured across the contacts 26a-26e of the electrode layer 24 are referred to as "short-leads" to distinguish them from the standard contact lead configuration "standard-leads" or "long-leads", which are ECG measurements obtained from the electrodes 16a-16d and 18a-18f in FIG. 1(g). The electronic patch layer 22 includes all of the electronics for performing the measurements which can be integrated into a single micro-chip. The plurality of contacts (preferably two or three) represented by 26f and 26g on the electronic patch layer 22 can be used at calibration time to connect a plurality of remote long leads (preferably two or three) via an external or extended lead wire. When connected, contacts 26f and 26g act as the reference electrode of the patch to the standard long-lead electrodes which allow acquisition of referential unipolar channels. For example, to obtain a bipolar channel such as Lead I, one can subtract the two referential leads 26f-16a (LA) and 26g-16b (RA). Because this calibration step is done only briefly, the connecting lead to the standard electrodes locations can be to made to standard adhering electrodes placed at these locations, or preferably the extended leads have non-adhering conductive surface at its end that allows to measure the bio-potentials as it temporarily comes in contact with the surface of the skin for a short time (about 5-10 secs). The reference used for measuring the long leads can be different from the reference used to measure the short leads, or alternatively it can be the same reference contact point.

FIGS. 2(a) through 2(g) depicts various configurations of the disposable electrode layer 24 each having a plurality of contact points 26 arranged on its surface. The electrode layer 24 can be made from a conductive contact that is contacting the skin with an impedance matching conductive layer such as silver-silver chloride gel (AgCl) and an adhesive layer to attach to the skin, in conventional fashion as regular ECG electrodes would be, except the electrode layer 24 of the present invention has multiple contact points or contacts 26a-26e on the same electrode layer instead of a single contact point. A plurality of ECG channels can be measured from the single electronic patch layer 22 attached to the electrode layer 24 in the "short-lead" configuration.

As a wireless device, the electronic patch layer 22 has to conserve all available battery power during operation and that means using power efficient electronics components, and design, as well as computationally efficient software subsystem and algorithms. LED lights may be provided on the surface of the patch layer to communicate information to the patient such as to indicate connectivity link status, patch grouping status, or additionally to indicate alarm or operational status of the electronic patch layer. Further, LED color and/or LED blinking and/or speaker sound annunciation and/or display and/or wireless transmission of information can all be used in various ways as a means of indicating such as operational status or alarms or user instructions for calibration process or history of use and records of interest in memory.

FIGS. 1(a) through 1(f) depict various preferred locations that a plurality of electrode assemblies 20 of the present invention may be placed on a patient's body 12. The multi-contact bio-potential electrode assembly 20 is preferably placed on top of the cardiac area on the surface of the patient's skin for the strongest possible signal with rich informational content, as shown in FIG. 1(b). Orthogonal "short-lead" directions produce signal content that is not redundant but independent and richer in its content.

In another embodiment, a plurality of electrode assemblies 20 can be placed in proximity to the heart area but not necessarily directly on top of it, for example, next to or near the side of the heart, off from its central position, as shown in FIG. 1(a). Similarly, when being used for females, the electrode assembly can be placed more comfortably on top of the breast surface rather than underneath it. In still another embodiment the electrode assembly can be placed anywhere else on the skin, such as the torso, left shoulder, right shoulder, right or left hip area (FIG. 1(c)), or the back of the body such as the back shoulder or the back of the cardiac area on the skin. This flexibility of positional location of the electrode assembly attachment adds significant advantages in the comfort of use of the ECG measurement patch, thereby not restricting its placement. The leadless ECG measurement system of the present invention importantly does not require extension of lead wires (such as wires 32a, 32b shown in FIG. 3) to remotely distant electrodes during the continuous measurement phase, but only during the brief calibration phase.

The plurality of electrode assemblies (at least one) include an electronic patch layer preferably enabled with wireless transceivers for wireless communication with a remote wireless base station or for wireless communication across the plurality of electrode assemblies. In a preferred embodiment, the plurality of electrode assemblies and base station operate, preferably, in a known-in-the-art wireless mesh network topology (for example, as enabled using Zigbee wireless transceivers). In another preferred embodiment, the plurality of electrode assemblies and base station operate, preferably, in a known-in-the-art wireless star network topology (for example, as enabled by either Zigbee or Bluetooth wireless transceivers) enabling electrode assembly communication with a single base station. The mesh network topology has the added advantage of robustness and redundancy of communication pathway between the plurality of electrode assemblies and the remote base station as compared to the star network topology. In a mesh network, if communications between one or more wireless electrode assemblies with the remote monitor were lost, perhaps due to fading or interrupted RF channel pathway, then these electrode assemblies will try to communicate their data via any of the remaining communicating wireless electrode assemblies. A plurality of electrode assemblies can share information about the measured or estimated bio-potentials such as short-leads, or long-leads, or produced transfer function, or other useful information with each other or with the base station.

Figure 3:
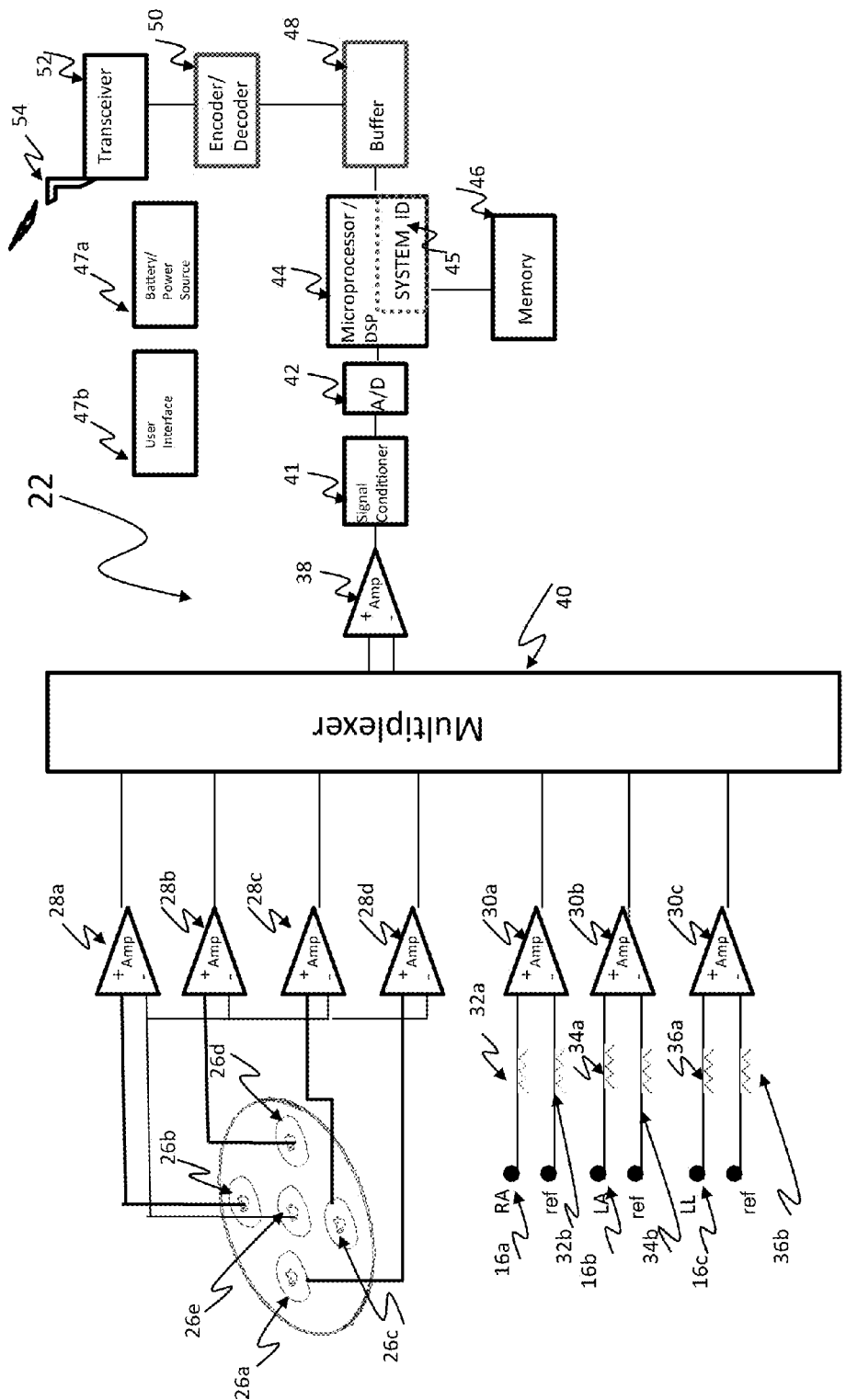
FIG. 3 is a block diagram of the electronic patch layer of FIGS. 1 and 2.

In FIG. 3, there is shown a block diagram of the electronic patch layer 22 of FIG. 2 connected with the plurality of contacts 26a through 26e of the disposable electrode layer 24. The electrical heart-signals defining the "short-lead" signals from the plurality of contacts 26a, 26b, 26d and 26e are supplied to a first input of a respective pre-amplifier stage 28a through 28d. The contact 26c provides a ground reference and is connected as a second input to each of the pre-amplifier stages 28a through 28d. Also, the heart signal defining the "standard-lead" or "long-lead" signal from the electrode 16a (FIG. 1(g)) and a reference signal are connected to a pre-amplifier stage 30a via external lead wires 32a and 32b. The heart signal defining the "standard-lead" or "long-lead" signal from the electrode 16b (FIG. 1(g)) and the reference signal are connected to a pre-amplifier stage 30b via external lead wires 34a and 34b. The heart signal defining the "standard-lead" or "long-lead" signal from the electrode 16c (FIG. 1(g)) and the reference signal are connected to a pre-amplifier stage 30c via external lead wires 36a and 36b.

The outputs of the pre-amplifier stages 28a-28d are fed to a high-gain amplifier 38 via multiplexer 40. The analog signals from the output of the high-gain amplifier 38 is fed to a signal conditioner 41 consisting of a high pass filter for baseline offset removal, a sampling anti-aliasing low pass filter, and a noise notch filter, and then to an a A/D converter 42 where they are filtered, sampled and converted to digital signals. These digitized signals are supplied to a microcontroller/Digital Signal Processor 44, which includes a System ID Processing device 45. Similarly, the outputs of the pre-amplifier stages 30a-30c are fed to the signal conditioner 41 and the A/D converter 42 via the multiplexer 40.

The System ID Model Processing device 45 performs a mapping function which relates the plurality of input measurements ECG "short-lead" waveforms vectors (from the pre-amplifier stages 28a-28d) with the plurality of output standard "long-lead" ECG waveform vectors (from the pre-amplifier stages 30a-30c). The identification system model structure, order and parameters describing the system relationship between the input "short-lead" signals and the output "long-lead" signals are stored in a memory 46. The microcontroller or digital signal processing unit 44 also processes commands and messages from the receiving base station 14 and executes programmed instructions stored in the memory 46. The processed digital ECG signals are then sent to a buffer 48 and an encoder/decoder 50 which are fed to a RF transceiver module 52 for transmission to the base station 14 via a low power built-in RF antenna 54. A battery/power source 47a is operatively connected to the various components for supplying DC power. A user interface 47b is provided which includes buttons, LEDs, or a display screen to permit a user to control and input various desired commands.

As should be clearly understood by those skilled in the art, for each such "short-lead" measurement, a minimum of three contacts are required to make a bipolar measurement (a positive contact, a negative contact, and a reference contact). The bio-potential at each of the contacts 26a-26e are presented to the amplifier 38 similar to the normal standard ECG measurement, however, the gain of such "short-lead" amplifier may be higher than the gain of standard lead amplifiers. Typical voltages detected across "short-leads" will be in the order of 10's to 100's of microvolts, while in standard "long-leads" (longer leads) the voltages will be generally from 1 millivolt to 10's of millivolts. It will also be understood the amplifiers 28a-28d and the high gain amplifier 38 can be configured to operate as a conventional instrumentation amplifier.

Figure 4:
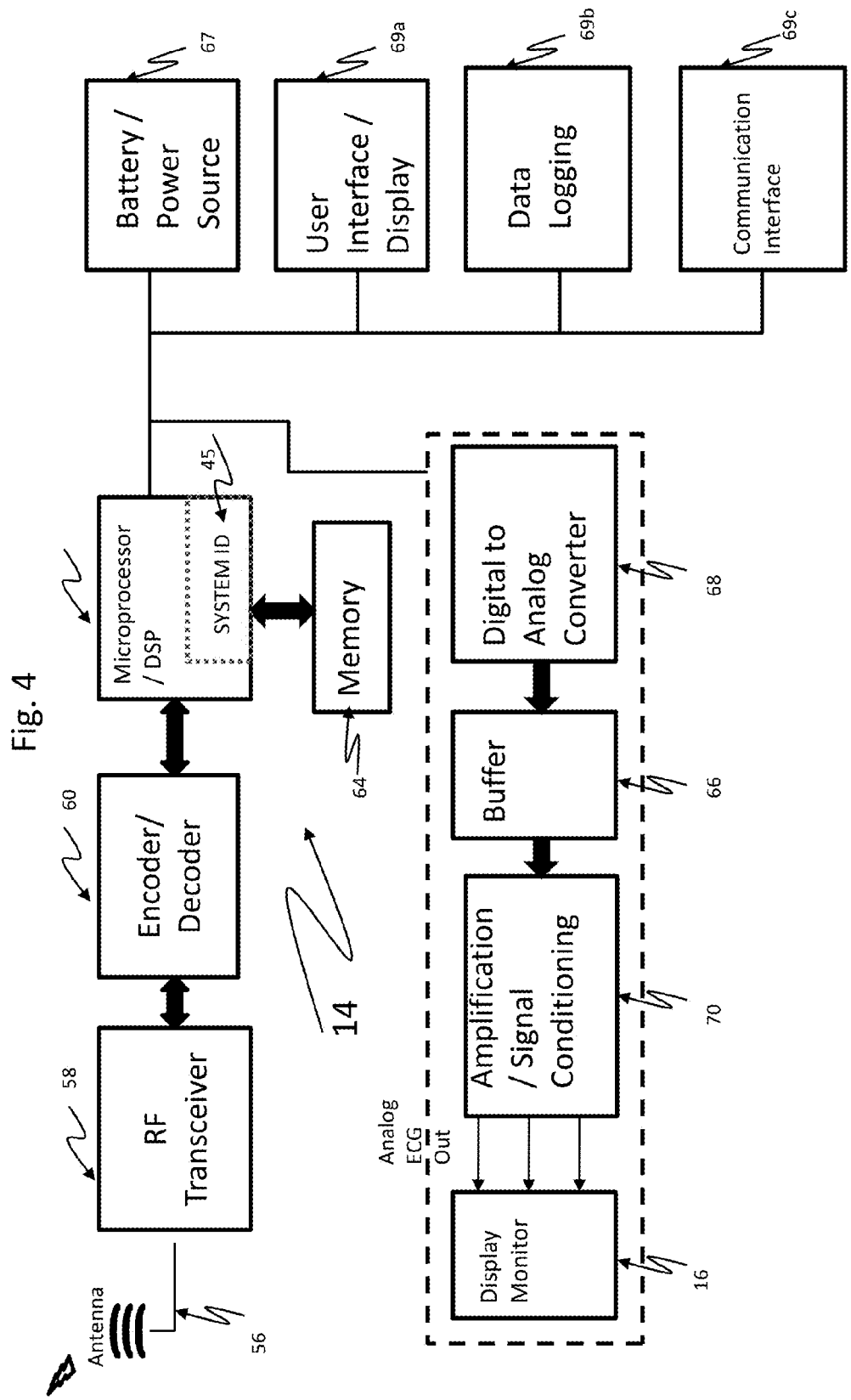
FIG. 4 is a block diagram of the base station of FIG. 1.

With reference to FIG. 4, there is shown a block diagram of the receiving base station 14 of FIG. 1. The base station 14 includes a low power RF antenna 56. In one embodiment, the base station 14 receives the transmitted "measured short-leads" digital ECG signals from the multi-contact electrode assembly 20. Optionally, the base station 14 receives the "measured long-leads" digital ECG signals from the electrodes 16a-16c (18a-18f) in FIG. 1(g) during calibration. In another preferred embodiment, the base station 14 receives the transmitted "estimated long-lead" digital ECG signals from the multi-contact electrode assembly 20. In FIGS. 11(a)-11(d), there are provided depictions of the mapping of short-leads to measured standard long-leads Lead I, Lead II, and Lead II producing a transfer function, preferably a linear state-space model in MISO structure, that outputs estimated long-leads based on short-leads only. The base station also includes a RF transceiver module 58 coupled to the RF antenna for receiving the processed digital ECG signals and feeds them to an encoder/decoder 60. A microcontroller/Digital Signal Processor (DSP) 62 is connected to the output of the encoder/decoder 60 for processing the digital ECG signals based on the programmed instructions for execution stored in a memory 64. The digital ECG signals from the microcontroller are supplied to a D/A converter 68 and a buffer 66 so as to convert the digital data to an analog form. The analog signals are sent to an amplifier/signal conditioner 70 and then to the ECG monitor 16 where the signals are treated as if they were generated from the standard ECG "long-lead" wire electrodes.

A battery/power source 67a is operatively connected to the various components for supplying DC power. A user interface device 69a is operatively connected to the microcontroller/DSP 62 to permit the user to control and input the various desired commands, wherein the user interface can also include a display monitor for displaying such received signals and derived valuable information as well as alerts and configuration information, and status information of the plurality of electrode assemblies. A data logger 69b allows saving of all system information to persistent memory/hard drive. A data communication interface 69c allows communication of all available digital information to external systems, including for example transmission of information via the internet or over TCP/IP protocols, or over cellular mobile networks, or local wireless networks.

While the System ID Model Processing device 45 is illustrated as being located in the microcontroller/DSP 44 of the electrode assembly 20, the System ID Processing device 45 shown in phantom may be located alternatively in the microcontroller/DSP 62 of the receiving base station 14 in order to reduce the size requirement of the power supply needed for the electronics in the patch layer 22 of the electrode assembly. The System ID Model Processing device 45 produces a system model which can be identified adaptively for each patient using two methods: (1) direct system identification and (2) blind system identification.

The direct system identification method is by application of conventional system identification methods for identifying adaptively the transfer function or mapping model relating the two waveform vectors between the "short-lead" measurement and the standard ECG "long-lead" measurement. By treating the "short-lead" signals as an input (stimulus) to a system with a certain transfer function characteristics that maps the input to a desired output (response) representing the standard "long-lead", a variety of conventional system identification tools can then be applied for determining the optimal system order, system structure, and parameter values describing the system relationship adaptively.

While there are available many tools and system identification strategies, the preferred embodiment of the present invention utilizes a direct system identification which uses state space methods, and preferably in a multiple input single output (MISO) configuration, as more fully discussed below. The state-space MISO system identification allows implementation of system identification methods in the novel application of leadless ECG measurement, and extends the science of system identification to the realization of a feasible leadless ECG application.

Figure 5:
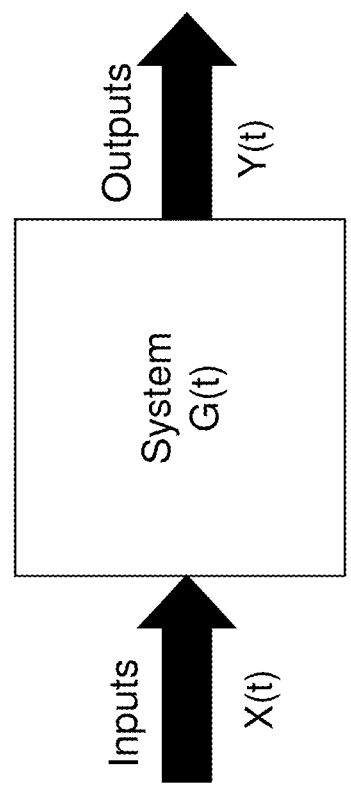
FIG. 5 is a system transfer function which illustrates the time domain and frequency domain relationships between the input and output time series.

In FIG. 5, there is depicted a system transfer function G(t) which illustrates the relationships in the time and frequency domains between the inputs X(t) and outputs Y(t). As can be seen, in the time domain the inputs X(t) are convoluted with the transfer function G(t) to produce the outputs Y(t). On the other hand, in the frequency domain the inputs X(f) are simply multiplied in order to obtain the outputs Y(f). Equivalently, any linear transfer function can be represented in different linear models structures or forms including non-parametric models (impulse response, frequency response) or parametric models (such as state-space, transfer functions, and polynomial models including Auto-progressive AR, Auto-regressive with noise ARX, Auto-regressive Moving Average ARMA, Auto-regressive Moving Average with noise ARMAX, Box Jenkins, Output Error, Generalized Linear) that describes. In a preferred embodiment, the linear state-space model structure representation of the transfer function and state-space model identification function allows ease of adaptation of the system model using a change to its model order to optimize its approximation or estimation of the system outputs, given its system inputs.

The state space models (reference 4 to Kailath in the Appendix) are defined as $$x(k+1)=Ax(k)+Bu(k)$$

$$y(k)=Cx(k)+Du(k)+n(k)$$

Where u(k), y(k), and x(k) are time series of real numbers representing the input, output, and state, respectively, of the system, and n(k) is time series of real numbers representing the noise term which is assumed to be independent of the input sequence u(k). A, B, C, and D indicate the coefficients vectors.

By using the Fourier transform on both sides of both equations of the state space model, we obtain the following, where sup. indicating superscript, and exp. indicates the exponent:

$$(\exp.^{jw})X(w)=AX(w)+BU(w)$$

$$Y(w)=CY(w)+DU(w)+N(w)$$

Where w is the frequency term, j indicates an imaginary number, and Y(w), U(w), X(w), N(w) are the frequency transformed output, input, noise, and state variables. The variables A, B, C, D indicate the coefficients vectors. Where $$G(\exp.^{jw})=G(z) \text{ at } z=\exp.^{jw}=D+C((zI-A)^{.\sup.-1})B \text{ at } z=\exp.^{jw} \text{ and,}$$

$$Y(w)=G(\exp.^{jw})U(w)+N(w)$$

is the frequency response function (FRF) of the system. I represents the identity matrix and sup.−1 represents a matrix inverse.

It will be noted that many other conventional System Identification methods exist and can provide substantially equivalent implementations to the state-space methods preferred in the present invention. These include (a) linear system identification (SYSID) methods, (b) nonlinear system identification methods, and (c) blind system identification methods. The background of each is discussed in details with algorithms describing prior art implementation details of such methods. The methods described apply for SISO (single input single output), MISO (multiple input single output), SIMO (single input (stimulus) multiple outputs (responses)), and MIMO (multiple inputs (stimuli) multiple outputs (responses)) configurations. This instant invention can equivalently, without loss of generality, use any of the other system identification methods mentioned below, and in any configuration of the inputs and outputs mentioned previously.

For example, as described in the references 1 through 6 listed in the Appendix which describe linear systems estimation and system identification methods, which are incorporated herein by reference, the linear SYSID parametric and non-parametric methods include:

AR
ARX
ARMA
ARMAX
Generalized Linear
Output Error
Box-Jones
Continuous transfer function
Discrete transfer function
Impulse realization
User defined model Principal components subspace identification
Discrete frequency transfer function from frequency response function
Continuous frequency transfer function from frequency response function
Maximum likelihood methods
The nonlinear SYSID methods include:
Neural Networks
Fuzzy Logic
Volterra Series
Weiner models (LMS, or recursive least square based)
Wavelets analysis
Nonlinear state-space models
The blind system identification methods include:
Laguerre model based
Deconvolution methods The system identification of the present invention can be either a SISO, if for example a single input channel was mapped to a single output channel, or, preferably, a MISO if the identified system was determined by mapping (or relating) multiple input channels (stimuli, measured "short-leads") into a single output channel (response, standard "long-leads"). Multiple inputs mapping provides greater informational content and therefore a better mapping accuracy to the output. Alternatively, a MIMO configuration can be used where the input measured signals ("short-leads") are used to calculate multiple output responses (standard "long-leads") in a single application of system identification methods rather than multiple applications of multiple subsystem identifications. Alternatively, a SIMO configuration can be applied where a single "short-lead" is used as an input to determine system relationship with multiple outputs (standard "long-leads").

Furthermore, the new calculated output leads from the primary systems identified can also be used as inputs (stimuli) into other secondary identified transfer functions relating them to other outputs (response, standard leads). This process can be again repeated for determining tertiary identified transfer functions, etc. as needed. However, with each such transfer function estimation, using estimates to calculate further estimates degrades the quality of the overall estimation. The overall final transfer function will be a multiplication (in the frequency domain) of all the primary and secondary stage transfer functions.

Recursive modeling builds towards an optimal total model, which involves predicting a model and using the predicted model output as input (stimulus) into predicting another model. To accomplish this, the first model has to be identified with high confidence and quality yielding excellent goodness of fit of model predicted outputs and actual outputs. Optimal models identified in the first stage will avoid the build up of errors and avoid rapid degradation of prediction quality in the identification of subsequent secondary models and the estimation of their responses.

Figure 6:
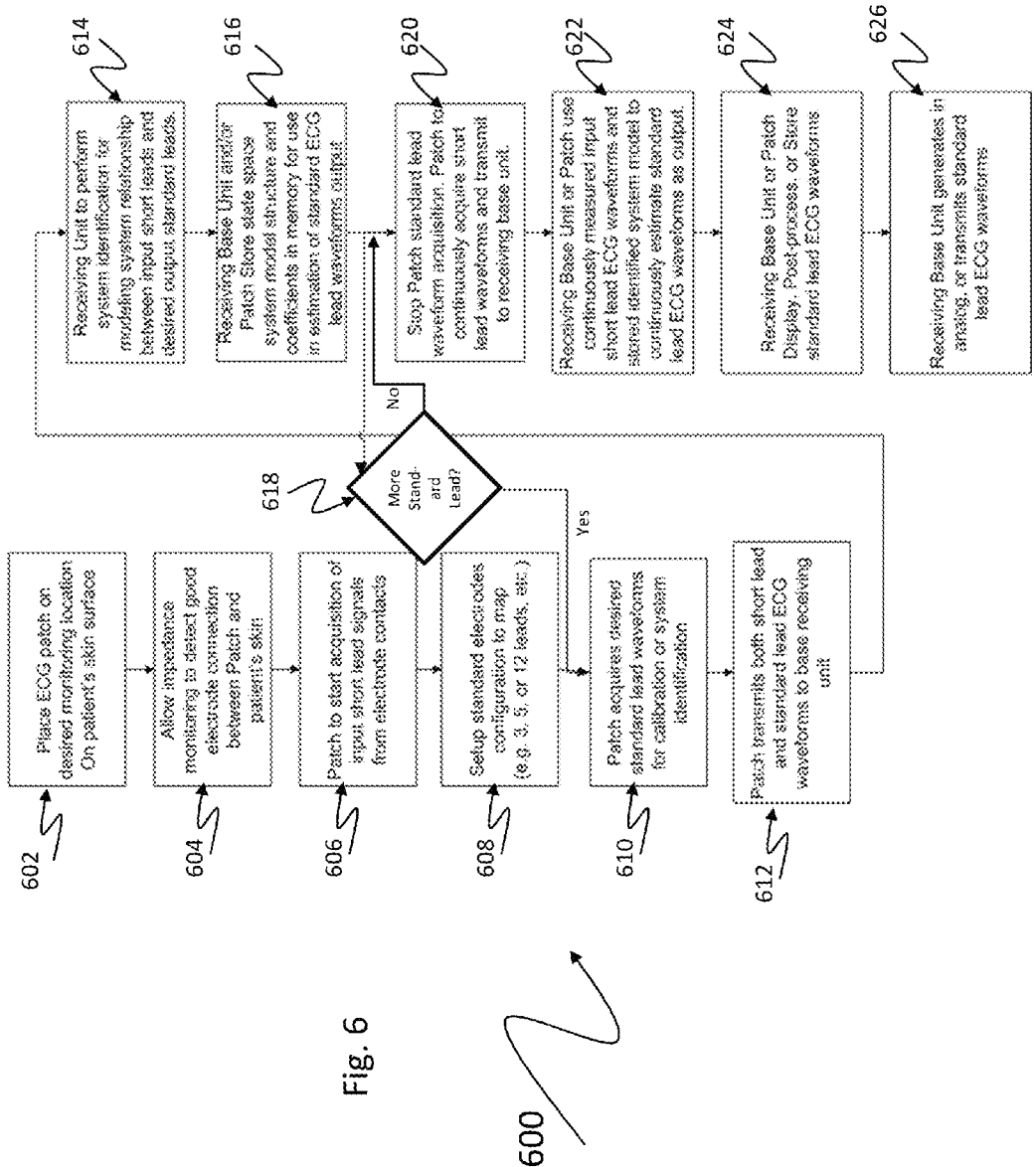
FIG. 6 is flow diagram of an exemplary embodiment of a calibration procedure.

FIG. 6 shows a flow diagram 600 of calibration procedure for use where the standard "long-leads" are used as outputs for the direct system identification device. Initially, at step 602 the electrode assembly 20 is placed or attached on a desired location on the patient's skin, as shown in FIGS. 1(a)-1(f). At step 604, impedance monitoring is allowed to determine if a good electrical connection has been established between the electrode layer 24 and the patient's skin. At step 606, the electrode assembly 20 starts the ECG data acquisition of the input "short-lead" signals. Alternatively, the receiving base station 14 instructs all of the electrical contacts, such as 26(a)-26(e) on the electrode layer 24 in FIG. 2 to start the ECG data acquisition of the input "short-lead" signals. The step 606 may be initiated in response to a user prompt by means of any suitable user interface, such as device 69a associated with the receiving base station 14 in FIG. 4 or the user interface 47b on the electrode assembly 20.

At step 608, at least two of the standard electrodes 16(a)-16(d) and 18(a)-18(f) at the locations shown in FIG. 1(g) are used to obtain a calibration waveform substantially simultaneously to obtaining a "short-lead" signal during the process of calibration or system identification of the transfer function in the signal processor residing either in the receiving base station 14 or in the electrode assembly 20 is configured to map the number of "long-leads" used in the standard ECG system, such as 1, 3, 5, or 12 leads with the locations of the standard electrodes. Again, the configuration can be achieved through the user interface device 69a associated with the base station 14 or the electrode assembly 20. In step 610, the electrode assembly 20 acquires desired standard "long-lead" waveforms used for calibration or system identification. At step 612, the electrode assembly 20 transmits substantially simultaneously both the "short-lead" and the standard "long-lead" ECG waveforms to the receiving base station 14 for calculation of the transfer function system identification model.

In particular, in one embodiment, one extended lead wire connecting the electrode assembly 20 at the contact point 20a (or optionally 20b) to any of the standard electrode locations on the body 16(a)-16(d) and 18(a)-18(f) in FIG. 1(g), can provide means for obtaining a referential (unipolar) voltage potential between the two contact points. The process is repeated at least once to obtain a second referential voltage potential with a second standard electrode body location. The results of the two referential potential measurements allow the calculation of the differential potential between the two standard contact points. Such differential (bipolar) potential represents one of the standard ECG bipolar "long-leads". If a "long-lead" is in fact unipolar, then a single referential measurement can represent such "long-lead". The process of measurement of the "long-lead" is repeated until all "long-leads" are mapped in the calibration process. In another embodiment, at least two extended lead wires each connecting the electrode assembly 20 at the contact point 20a or 20b to at least any two of the standard electrodes 16(a)-16(d) and 18(a)-18(f) at locations on the body in FIG. 1(g), can provide means for obtaining a differential (bipolar) voltage potential between the two contact points for each extended lead wire. This embodiment accelerates the calibration mapping process. An extended lead wire is preferably external to the device, or it can be tethered and retractable into the patch electrode assembly, since it is used only during the calibration process, and containing conductive contact ends suitable for placement on the skin's surface for measuring bio-potential. Each time a referential or differential bio-potential is obtained for a "long-lead", at least one "short-lead" bio-potential signal is also measured substantially simultaneously between any of the internal electrodes in the patch electrode assembly 20 that are in contact with the patient's skin. The contacts such as 32(a)-36(a) and 32(b)-36(b) in FIG. 3 are connected temporarily from the standard lead contact points 16(a)-16(c) to the measurement electronics of the patch layer 22 in the electrode assembly 20 so as to permit the acquisition of the standard "long-leads" and the short-leads" substantially simultaneously. The input "short-lead" ECG waveforms and the output "long-lead" ECG waveforms are alternately transmitted for a short period of time, e.g., about 5-10 seconds. This measurement is only needed for a brief time period, preferably a few seconds, for each "long-lead" in the desired configuration. The substantially simultaneously measured "long-lead" signals (outputs) and "short-lead" signals (inputs) are then processed by the signal processor to calculate the calibration transfer function or model, preferably in the form of a linear state-space model. In step 614, the base receiving station 14 performs system identification via the DSP 62 for modeling system relationship between measured input "short-lead" ECG waveforms and the desired output standard "long-lead" ECG waveforms.

The state space system model structure and coefficients are stored in the memory 64 associated with the base station 14 or in the memory 46 associated with the electrode assembly 20 in step 616 for use in the estimation of standard ECG "long-lead" waveforms. In step 618, it is determined whether there are additional standard leads to be measured. If the answer is "yes", then the steps 610 through 616 are repeated. If on the other hand, the answer is "no", the procedure will proceed to step 620.

In the step 620, acquisition of the standard "long-lead" waveforms from the electrode assembly 20 is stopped and the lead wires connected temporary between the standard lead contact points and the electrode assembly are then removed. Further, the electrode assembly 20 will then be configured to function in a continuous measurement operational mode, using the system identification model previously determined to continuously acquire "short-lead" waveforms and to transmit them to the receiving base station 14. In step 622, the receiving base station or the electrode assembly will use the continuously measured input ECG "short-lead" waveforms and the system identification model stored in memory to continuously estimate the output standard ECG "long-lead" waveforms. In step 624, the base station or electrode assembly will display, perform post-processing operations, or store the standard ECG "long-lead" waveforms. Finally, in step 626 the base station generates in analog form or transmits the standard ECG "long-lead" waveforms to the monitor 16 for displaying meaningful information to the physician or user.

Figure 7:
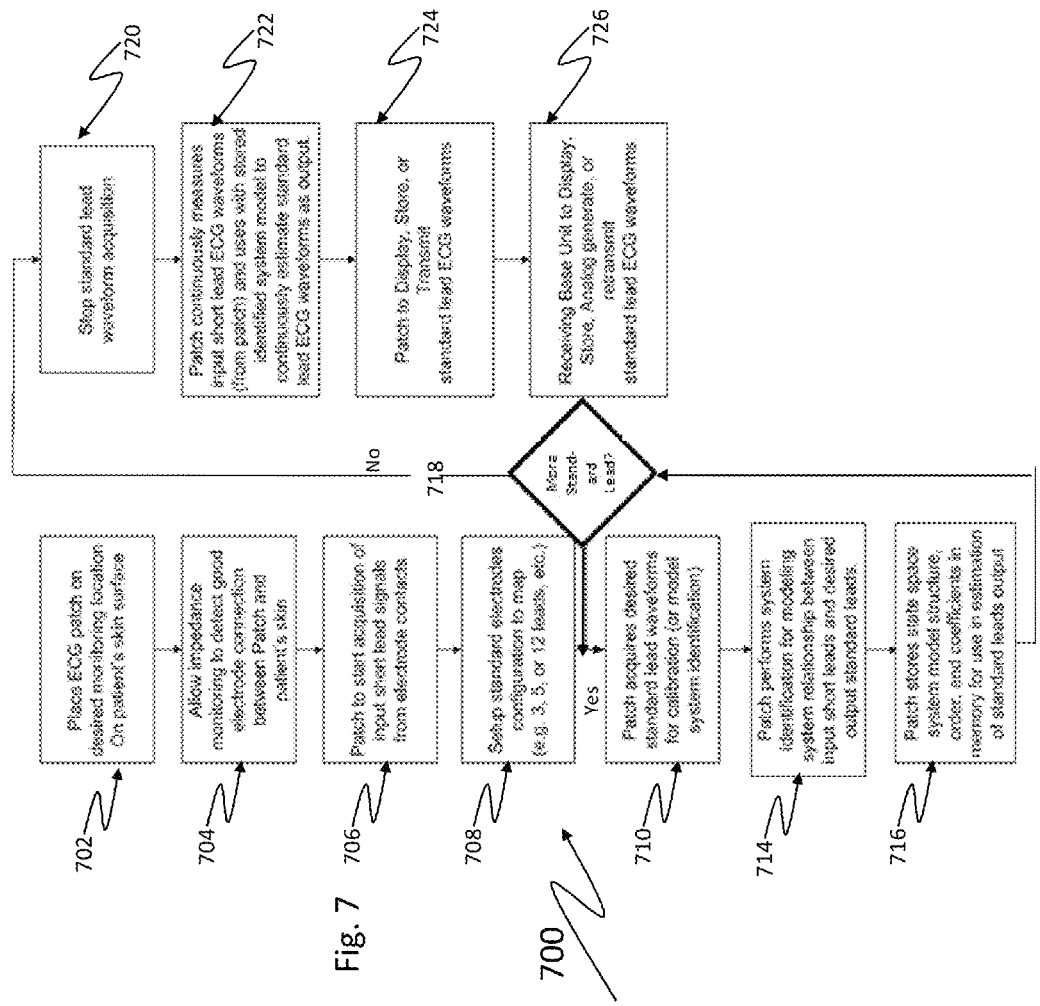
FIG. 7 is flow diagram of an exemplary embodiment of an alternate calibration procedure.

FIG. 7 depicts a flow chart 700 of an alternate calibration procedure for use where the standard "long-leads" are used as outputs for the direct system identification device. It will be noted that the calibration procedure of FIG. 7 is substantially identical to the procedure of FIG. 6, except that the system identification for modeling system relationship between the input "short-leads" and the desired output "standard-leads" is performed in the electrode assembly 20 instead of in the base station 14.

Specifically, at step 702 the electrode assembly is placed or attached on a desired location on the patient's skin. At step 704, impedance monitoring is allowed to determine if a good electrical connection has been established between the electrode layer and the patient's skin. At step 706, the electrical contacts on the electrode layer start the ECG data acquisition of the input "short-lead" signals. The step 706 may be initiated automatically by the electrode assembly 20 or in response to a user prompt by means of any suitable user interface associated either with the electrode assembly or the base station.

At step 708, the standard electrodes are set up and the electrode assembly is configured to map the number of leads used in the standard ECG system, such as 1, 3, 5, or 12 leads. Again, the configuration can be achieved through the user interface associated with the electrode assembly or the base station. In step 710, the electrode assembly acquires desired standard "long-lead" waveforms used for calibration or system identification. In particular, extended lead wires are connected temporarily from the standard lead contact points to the measurement electronics of the patch layer in the electrode assembly so as to permit the acquisition of the standard "long-leads" and the short-leads" substantially simultaneously.

In step 714, the electrode assembly performs system identification via the DSP for modeling system relationship between measured input "short-lead" ECG waveforms and the desired output standard "long-lead" ECG waveforms. The state space system model structure and coefficients are stored in the memory associated with the electrode assembly in step 716 for use in the estimation of standard ECG "long-lead" waveforms. In step 718, it is determined whether there are additional standard leads to be measured. If the answer is "yes", then the steps 710 through 716 are repeated. If on the other hand, the answer is "no", the procedure will proceed to step 720.

In the step 720, acquisition of the standard "long-lead" waveforms from the electrode assembly is stopped and the lead wires connected temporary between the standard lead contact points and the electrode assembly are then removed. Further, the electrode assembly will be configured to function in a continuous measurement operational mode, using the system identification model previously determined to continuously acquire "short-lead" waveforms. In step 722, the electrode assembly will use the continuously measured input ECG "short-lead" waveforms and the system identification model stored in memory to continuously estimate the output standard ECG "long-lead" waveforms. In step 724, the electrode assembly will display, perform post-processing operations, or transmit to the base station estimated standard ECG "long-lead" waveforms. Finally, in step 726 the base station will display, store, generates in analog form or re-transmits the estimated standard ECG "long-lead" waveforms to the monitor for displaying the waveforms and related meaningful information to the physician or user.

If degradation in quality of the reported standard lead signal estimation necessitates a recalibration step being necessary, due to a recommended time duration from a previous calibration being exceeded, or substantial change in impedance values monitored by the electrode assembly, or due to repositioning, removal, and replacement, of the electrode assembly. The system identification model can also allow reuse of previous calibration models, inputs and/or outputs stored in memory for comparative purposes of quality of signal, identifying changed components, or for accepting a previous or new calibration for continuous operation purposes.

Figure 8:
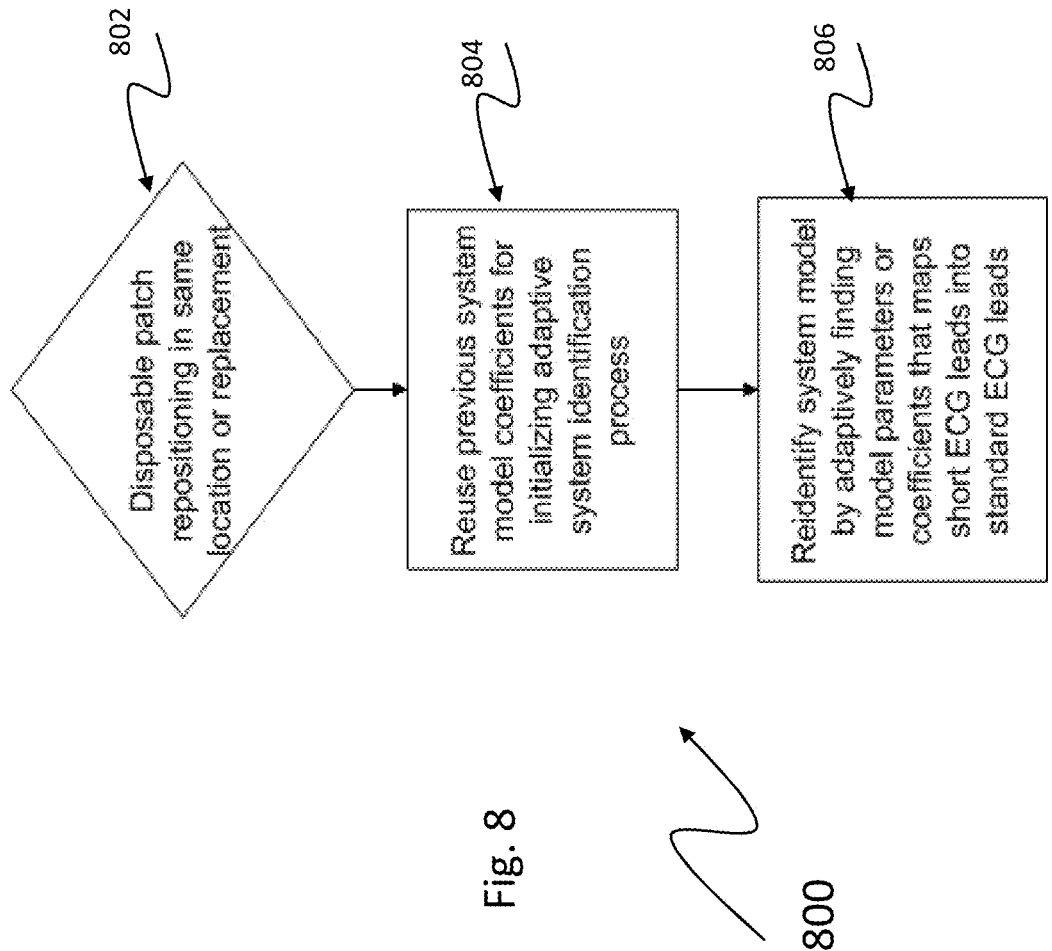
FIG. 8 is flow diagram of an exemplary embodiment of a re-calibration procedure.
Figure 9:
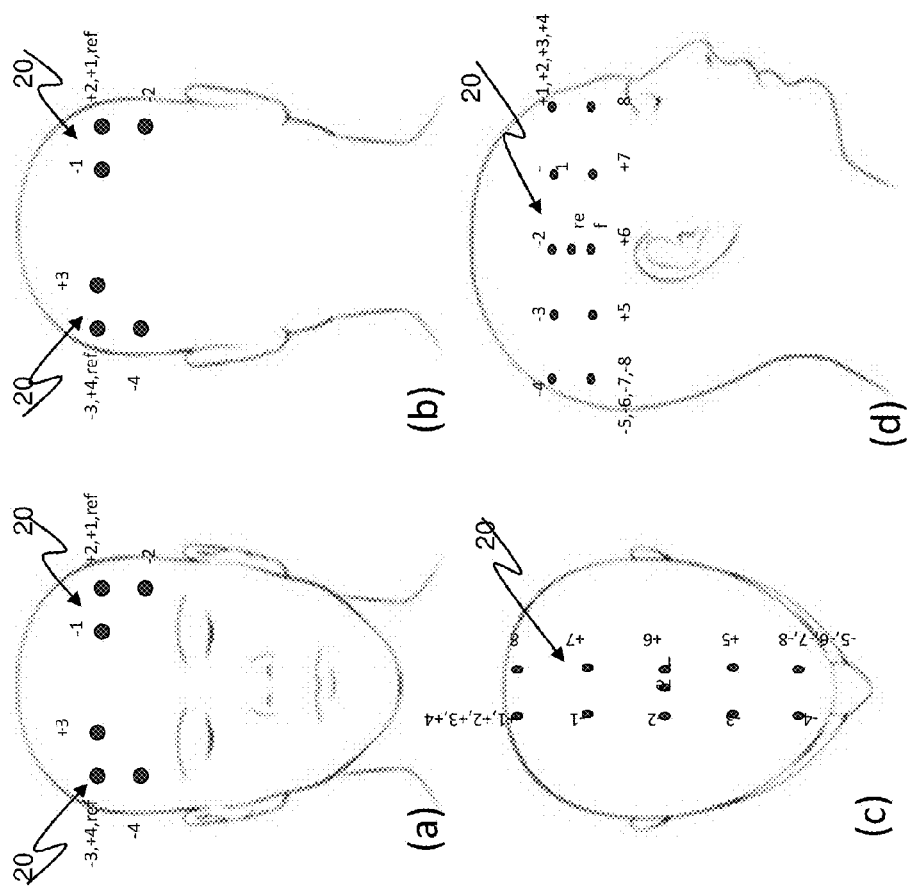
FIG. 9(a) through 9(d) depict various locations that the electrode assembly may be placed on the head's scalp surface of a patient.

In FIG. 8, there is illustrated a flow chart 800 of a re-calibration procedure system model which re-uses previously identified system model parameters or coefficients as an initialization point to the new model system identification process. In other words, new system model parameters are found by beginning with the old system as the initialization point. In particular, in step 802, the disposable electrode layer is re-positioned in the same location on the patient's body. In step 804, the previous system model coefficients are re-used for initializing adaptive system identification process. In step 806, the previous system model created by adaptively finds model parameters or coefficients that maps the ECG "short-leads" into the standard ECG "long-leads" are re-identified.

This recalibration procedure facilitates to identify systems that are fairly similar yet slightly optimized to meet better quality estimation requirements of the output standard "long-leads". Furthermore, it is possible to constrain the estimation of the system parameters identified within a reasonable range from the previously found system parameters (with upper and/or lower boundary limits), in order to avoid divergence to an unacceptable state of the identified system.

The leadless wireless ECG measurement system and method of the present invention has the following advantages over the prior art as follows:

(1) it provides clinical equivalence to standard lead ECG measurements;
(2) it utilizes a personalized per patient calibration so as to ensure accuracy;
(3) it reduces cost to the patient and health care giver, and reduces time for care giver to sort out wires;
(4) it reduces substantially motion artifacts due to elimination of leads (especially for Holter monitoring and stress monitors);
(5) it reduces opportunities for infection due to wires exposure to body fluids;
(6) it increases comfort for patients by elimination of wires;
(7) it eliminates leads-off alarms due to tugged wires;
(8) it eliminates wrong lead connection attachment;
(9) it produces a standard multiple-lead ECG with a single wireless patch application, thereby reducing number of leads required to produce a fully diagnostic 12-lead, 5-lead, or 3-lead ECG; and
(10) it produces potential expansion markets which include Stress ECG monitoring, Holter monitoring, and continuous surface ECG monitoring via implanted Pacemakers or internal and external defibrillators.

From the foregoing detailed description, it should be clearly understood that the leadless ECG measurement system is composed of at least one multi-contact electrode assembly attached to the patient body and a remote monitor in communication with the at least one multi-contact electrode assembly. The electrode assembly includes an electrode layer with a plurality of contacts for contacting the skin's surface on the patient, preferably made of flexible membrane polymer, for comfortable fit to the skin's curvature, and an electronic patch layer disposed on top of the electrode layer, to which the electronic components are mounted.

This system of the present invention can also be used as just an add-on or supplementary to the standard measured 12-lead ECG system, as an enhancement providing substitute lead estimation to measured leads when needed. For example, in case we loose a lead's contacts (e.g. electrode peals off) or a lead experiences motion or noise artifacts in the signal, then we can compensate for the measurement noise error (suppressing its presence) or completely replace the faulty measured standard lead with a calculated estimate of that standard lead. The estimates can be derived by using data from other good standard leads as inputs and identified models relating these inputs to the faulty output signal now being estimated. This strategy enhances the acquisition of standard 12-lead ECG by making it more robust to noise factors. In other words, leadless ECG algorithms and methods can be used as an auxiliary to existing ECG platforms and not just as a stand-alone platform.

Integration of algorithms for detection, recognition, classification, and alerting of abnormal ECG patterns including Arrhythmia ECG, Bradycardia ECG, Tachycardia ECG, Atrial or ventricular fibrillation, Alternan ECG, etc. can be done to enable such active detection of abnormalities and alarming against such events. The electronic patches can optionally have an alarm speaker that delivers the alarm, or can transmit the alarm status to the wireless communication monitor if connected for further annunciating the alarm, or email messaging the alarm status and information which may include a sample of the abnormal digital ECG waveform data for immediate viewing of the alarmed abnormal ECG segment, or telephoning an emergency contact phone number with the alarm message, or text messaging the alarm message to a text message receiving phone number. Alternatively the alarm events can be stored in memory in case there was no communication link to the remote monitor. Cross-referencing of all event information across the electronic patches can also occur to match events detected independently on each of the electronic patches, if applicable. A table of such cross-referencing events can be generated at the monitor, or the information can be equally indicated on a graphical representation of each of the channels/patches acquired or calculated channels. The monitor can also display a graphical approximate physical location of those acquired or calculated bio-potential channels represented relative to a human body diagram.

The discussion of the present invention has thus far focused mainly on ECG waveforms processing; however, it should be clearly understood that ECG is only one of several bioelectric physiologic signals of interest that are measured on the surface of the skin. Other signals of interest include electroencephalography (EEG), electromyography (EMG), electrooculography (EOG), and electrogram (EGM). Implanted pacemakers typically measure Electrograms (EGM) directly on the cardiac muscle (either internally or externally). A relationship system model can be identified mapping the input EGM into output surface ECG, in standard 12-lead configuration, can be obtained, thus providing continuous surface ECG monitoring by the pacemaker and simplifying the interpretation of EGM by clinicians, regardless where the placement of the pacing electrodes on the cardiac muscle was. The surface ECG view of cardiac muscle EGM offers a continuous diagnostic interpretation that is more intuitive to an otherwise more difficult to interpret EGM signals. Depending on where the affected cardiac tissue is, and where the placement of the measuring leads contacts are, an EGM may offer different information for different patients, however, a surface ECG is a more common standard perspective for cardiac electric activity interpretation. Alternatively, evoked bio-potentials can also be used in identifying the system relating the evoked input(s) and the measured output bio-potential response(s). For example, the evoked input can include an optical light stimulation of varying intensity at a plurality of frequencies and amplitudes, or an auditory pulse or waveform at a varying plurality of frequencies and amplitudes, or an electric stimulation signal injected onto the skin or muscle typically of relatively higher voltage and low current characteristics (such as for EMG stimulation) also at a plurality of frequencies and amplitudes. In any form, the evoking signals can act as inputs while measured evoked bio-potentials can act as outputs, and the plurality of inputs and plurality of outputs are then presented to the system identification tools for model identification that provides best fit between estimated outputs and actual outputs.

Similar equivalent arguments to the entire discussion and spirit of the present invention of leadless ECG, can be applied to these other bioelectric physiologic signals of neurological interest. The spirit of this instant invention, without loss of generality, can be equivalently applied and extended to other frequency ranges or spectral bands, and topographic area of measurement to be applied to EEG, EMG, or EOG. Similar electronic components and wireless transmission protocols and informational exchange can be applied for measurement of such bioelectric physiologic signals.

More specifically, for leadless EEG (electroencephalogram) application the system, algorithms, and methods described above for leadless ECG can be extended to operate equivalently therefor with modifications required for operating frequency band, filtering frequency band, number of channels, and amplification gain to make it fit for EEG acquisition. In FIGS. 9(a) through 9(d), there are illustrated various locations that the electrode assembly of the present invention may be placed on the head's scalp surface of the patient. The leadless EEG device can equivalently be applied for the measurement of EEG as a bio-potential for the purpose of creating inter-channel mapping transfer functions (identified models) and therefore reduce a significant number of EEG leads (output channels) during EEG monitoring by providing estimated calculated EEG leads (outputs) using a minimal number of acquired short EEG leads (inputs). By reducing the number of required EEG channel from a full montage to one, two, or three channels, for example, one can substitute the measurement of the remaining EEG channels by a calculation of the estimated EEG for these channels using the minimal set of measured EEG channels as input and a plurality of identified system models relating the measured input channels with the remaining output channels.

Calculated standard lead EEG waveforms can be estimated using the input short lead EEG waveforms and a system model of transfer function relationship between the standard lead and the input short lead. The short lead used as input could also represent another standard lead itself. In other words, some of the standard leads can be used to act as short EEG leads and used as input into the system identification process in order to estimate the transfer function to other standard EEG leads. Therefore, with the models estimated available, a few EEG standard leads can be then measured, and the rest can be estimated with fairly high accuracy. This will allow for significantly reduced number of leads for acquisition of full EEG montage leads.

In addition, the conventional direct (linear or non-linear) or blind system identification method previously described can be applied in a novel application for monitoring of bio-potential activity generation sources in the brain. A plurality of measured bio-potentials on each hemisphere of the brain can be used adequately to estimate the generating source signals and location of the signals. This can be accomplished by using "short-lead" signals to estimate other leads as output of system identified models, then comparing the model output signals with actual measured signals from such modeled leads. The comparison yields difference signals representing unique or novel informational components for these channels while removing common informational components. This method can be used to isolate these components as being sourced from either the frontal lobe, or the posterior lobe, or from either the left hemisphere, the right hemisphere, or classified as being crossing over from one hemisphere to the other. Such segregation is important for isolation of the source of abnormal bio-potential activity, and then the determination of its location. Sources of abnormal bio-potential activity can include tumors, seizure activation sites, Parkinson source trigger tissue, and or effect of sedative medications on each of the hemispheres as well as aggregate effect estimation.

As thus far described, the leadless ECG system of the present invention models the patient's body's ability to conduct ECG and the effects of varying skin impedances. The identified parameters and models describe the transfer functions (system models) between the patient's measured bio-potentials at specific points on the surface of the skin (or internal to it if electrodes are subcutaneous or implantable). However, dynamic changes to these modeled parameters can also be indicative of the dynamic state changes in the patient's body over time, given fixed measurement positions of the electrodes contacts. Automated remodeling of the patient's transfer function (system model) relating the skin surface ECG's allows for dynamic noninvasive monitoring of the patient's body dynamics. Dynamic changes in the identified modeled parameters that describe the patient's body can be used as non-invasive indicators used to frequently monitor physiologic factors that influence such model parameters. Some of these factors are cardiac output, and hydration status level, and effects of induced vasoconstriction or vasodilatation of the vascular system.

Figure 10:
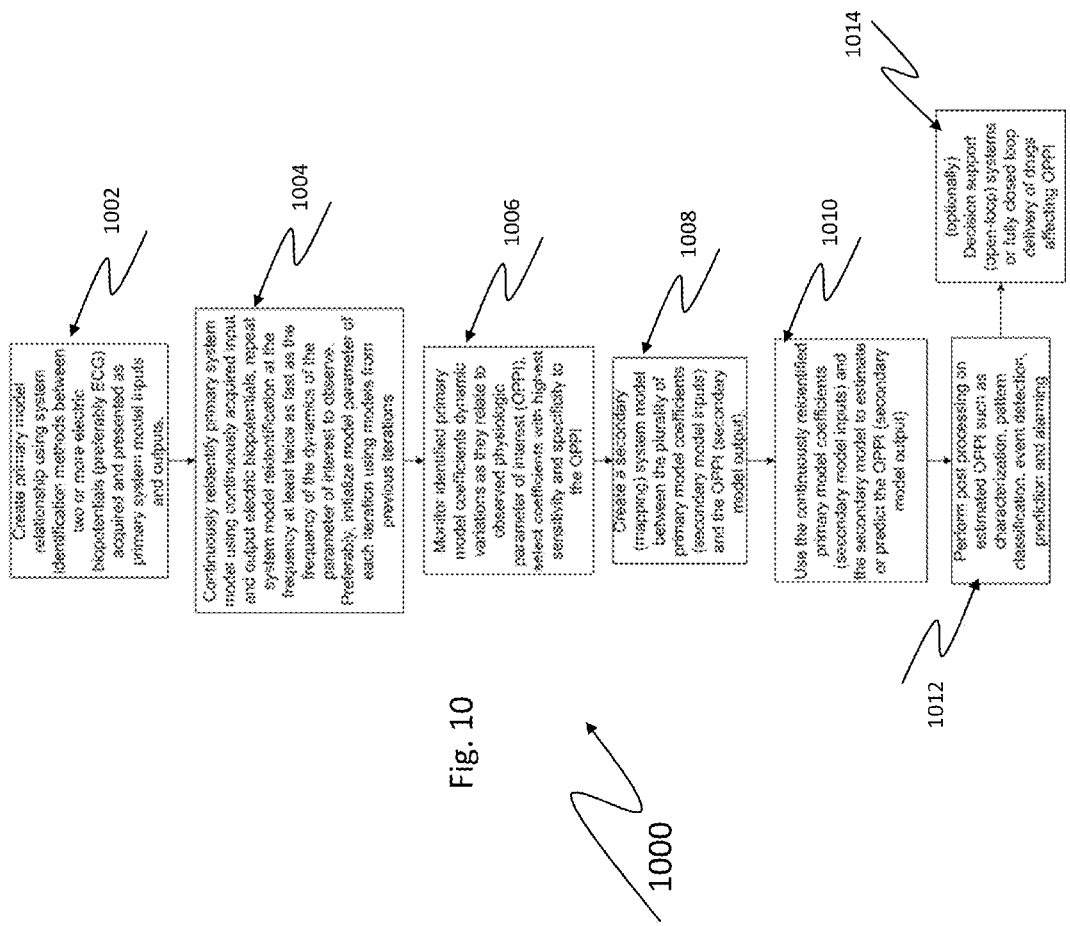
FIG. 10 is a flow diagram of an exemplary embodiment of a physiologic parameter monitoring procedure.

With attention directed to FIG. 10 of the drawings, there is illustrated a flow diagram 1000 of an exemplary embodiment of a physiologic parameter monitoring procedure for dynamic non-invasive monitoring of the patient's body dynamics. In step 1002, identification of a primary model (structure, and order) and its parameters (values) that best-fits a physiologic relationship between selected plurality of input physiologic variables or input analytic variables and selected plurality of output physiologic variables or output analytic variables is created. Such relationship between inputs and outputs has to be meaningful physically, chemically, or electrically for the model to reflect reality. Model optimization by selecting the right model order and model structure that minimizes output estimation errors from actual outputs is important.

In step 1004, repeatedly reidentifying the model parameters (using same model structure and order as primary) utilizing new information of the plurality of inputs and plurality of outputs at same measurement locations as before is continuously and repeatedly re-identified. Model re-identification occurs at a frequency and interval that are meaningful for the underlying model change. The model sampling frequency is required to be at least twice as fast as the expected change in dynamics of the model parameters in order to obtain representative reflection of the dynamic system changes that is presented in the model parameters variations. The previously identified model may always be used as part of the initial conditions for re-identifying the model parameters or optimizing its parameters goodness of fit as measured with estimated outputs difference from actual outputs.

Each of the parameters within the identified model structure for dynamic variations through time that are representative or correlating with the dynamic variations in target physiologic or analytic parameters of interest is monitored in step 1006. In other words, do any of the system model parameters reflect underlying system model changes (as opposed to input changes) that offer a correlating relationship with a target physiologic or analytic parameter. For example, the system relating a plurality of ECG waveforms describes or maps the underlying tissue electric properties and those properties changing through time may be correlated with a number of variables of interest. For example, a plurality of model parameters may offer more sensitivity and specificity to cardiac output or fluidic hydration status that is altering the electrical properties of the tissue within which the ECG is measured by variable hydration state. Another parameter of the identified model may offer more sensitivity or specificity to pain or stress experienced by oncology patients or patients undergoing surgery. Furthermore, another parameter of the identified model may offer greater sensitivity and specificity to glucose level in a patient.

In step 1008, a secondary identified model function is created so to relate a plurality of the primary model parameters with high sensitivity and specificity to the desired target physiologic or analytic parameter (or "observed physiologic parameter of interest"—OPPI). This allows one to effectively estimate and predict the desired target physiologic or analytic parameter using only the inputs and outputs required for the primary model identification and continuous re-identification at a selected frequency. For example, use ECG bio-potential waveforms input and output to monitor glucose, or respiration, or cardiac output, or hydration status.

In step 1010, For example, using ECG bio-potentials as input(s) and output(s) into the primary system identified model parameters, one can determine parameters with variations or dynamics that are most sensitive and/or specific to chest fluidic content, and can therefore use that for detecting abnormal events occurrence such as detection of congestive heart failure conditions. Similarly, one or more coefficients of the best fit system identified model, preferably state space, can be linked with its sensitivity and specificity to glucose as its concentration changes over time, and can therefore identify a relationship between the varying glucose concentration and variations to one or more coefficient(s) describing the system model underneath.

Such relationship between a desired observable (desired output) physiologic or chemical effect on the system represented by a variation of the (measured input) system model coefficients over time can further be well defined by a secondary system identification step relating the two input and output variables. Therefore, the primary system identification step 1002 provided a description of the physiologic and anatomic system between non-invasively measured bioelectric surface potentials, and the repeating of such system description provides insights into its variation over time due to some parameter that is desired to be observed. On the other hand, the secondary system identification step 1008 establishes such relationship between the varying system-identified coefficients of the model and the desired varying observable so that we can predict the later (as output) using the former (as input) into the secondary system-identified model.

Post processing on the estimated observed physiologic parameter of interest, such as characterization, pattern, classification, event detection, predication, and alarming is performed in step 1012. Finally, in optional step 1014 decision support (open-loop) systems or fully closed loop may be used to provide delivery of drugs affecting the observed physiologic parameter of interest.

While there has been illustrated and described what is at present considered to be a preferred embodiment of the present invention, it will be understood by those skilled in the art that various changes and modifications may be made, and equivalents may be substituted for elements thereof without departing from the true scope of the invention. In addition, many modifications may be made to adapt a particular situation or material to the teachings of the invention without departing from the central scope thereof. Therefore, it is intended that this invention not be limited to the particular embodiment disclosed as the best mode contemplated for carrying out the invention, but that the invention will include all embodiments falling within the scope of the appended claims.

Appendix

References:
1. System_Identification:_Theory_for_the_User, Lennart Ljung, Prentice Hall, 2nd edition, 1999.
2. System Identification: A Frequency Domain Approach Rik Pintelon and Johan Schoukens Wiley-IEEE Press, 1st edition, January, 2001
3. Blind Equalization and System Identification: Batch Processing Algorithms, Performance and Applications, Springer, 1st Edition, January 2006.
4. Linear estimation, Kailath, Sayed, Hassibi. Prentice Hall, 2000.
5. Multivariable System Identification For Process Control, Y. Zhu, Elsevier Science; 1 edition (October, 2001)
6. Modeling of Dynamic Systems, L. Ljung, Prentice Hall; 1 edition, May 1994.

The invention claimed is:

1. A leadless ECG measurement system for measuring of bio-potential electrical activity of the heart in a patient's body, comprising:
    at least one multi-contact bio-potential electrode assembly adapted for attachment to the patient's body, said electrode assembly being formed of an electronic patch layer and a disposable electrode layer;
    said disposable electrode layer having a plurality of contact points for engagement with the surface of the patient's body and configured to measure short-lead ECG signals in response to electrical activity in the heart; and
    a processing unit being provided and configured to produce a transfer function which computes estimated long-lead ECG signals based on the measured short-lead ECG signals from said plurality of contact points, said processing unit employing a system identification technique to define said transfer function.

2. A leadless ECG measurement system as claimed in claim 1, wherein a monitor is coupled to receive said estimated long-lead ECG signals for displaying said estimated long-lead ECG signals and other meaningful information.

3. A leadless ECG measurement system claimed in claim 1, wherein said leadless ECG system is wireless, said electronic patch layer includes a transceiver unit for transmitting and receiving wireless communications with a base station, and said base station includes a wireless transceiver for transmitting and receiving communications with said plurality of contact points in said disposable electrode layer, said wireless communications received by said wireless transceiver in said base station including said estimated long-lead ECG signals.

4. A leadless ECG measurement system as claimed in claim 1, wherein said at least one multi-contact bio-potential electrode assembly is in communication with at least a second multi-contact bio-potential electrode assembly, said communications including measured ECG signals, estimated ECG signals, transfer function, and other useful information.

5. A leadless ECG measurement system as claimed in claim 1, wherein said processing unit is disposed in said electronic patch layer of said electrode assembly.

6. A leadless ECG measurement system as claimed in claim 5, wherein said processing unit is comprised of a digital signal processor.

7. A leadless ECG measurement system as claimed in claim 1, wherein said processing unit is comprised of a digital signal processor.

8. A leadless ECG measurement system as claimed in claim 7, wherein said system identification technique uses linear state-space model identification.

9. A leadless ECG measurement system as claimed in claim 1, wherein said transfer function computes estimated long-lead ECG signals based on other estimated long-lead ECG signals and the measured short-lead ECG signals from said plurality of contact points.

10. A leadless ECG measurement system as claimed in claim 1, wherein said processing unit employs signal processing and analysis on said measured and estimated ECG signals to detect and declare abnormalities.

11. A leadless ECG measurement system as claimed in claim 1, wherein said electronic patch layer includes a plurality of electrical contacts for attaching a plurality of extended leads for measurement of a plurality of long-lead signals.

12. A leadless ECG measurement system as claimed in claim 1, wherein said long-lead signals represent standard ECG leads with standard electrode locations.

13. A leadless ECG measurement system as claimed in claim 1, wherein said electrode assembly is placed in proximity to the cardiac area, including being disposed next to or near the side of the heart.

14. A leadless ECG measurement system as claimed in claim 1, wherein said system is employed in conjunction with a standard ECG measurement system to improve performance against failed leads.

15. A leadless ECG measurement system as claimed in claim 1, wherein said estimated long leads are converted into analog output signals.

16. In a leadless ECG measurement system for measuring of bio-potential electrical activity of the heart in a patient's body, the improvement comprising:
    providing at least one multi-contact bio-potential electrode assembly for attachment to the patient's body, said electrode assembly being formed of an electronic patch layer and a disposable electrode layer;
    providing a plurality of contact points in said disposable electrode layer for engagement with the surface of the patient's body and configuring the plurality of contact points to measure short-lead ECG signals in response to electrical activity in the heart; and
    providing a processing unit and configuring the processing unit to produce a transfer function which computes estimated long-lead ECG signals based on the measured short-lead ECG signals from said plurality of contact points, said processing unit employing a system identification technique to define said transfer function.

17. The improvement of claim 16, wherein a monitor is coupled to receive said estimated long-lead ECG signals for displaying said estimated long-lead ECG signals and other meaningful information.

18. The improvement of claim 16, wherein said leadless ECG system is wireless, said electronic patch layer includes a transceiver unit for transmitting and receiving wireless communications with a base station, and said base station includes a wireless transceiver for transmitting and receiving communications with said plurality of contact points in said disposable electrode layer, said wireless communications received by said wireless transceiver in said base station including said estimated long-lead ECG signals.

19. The improvement of claim 16, wherein said at least one multi-contact bio-potential electrode assembly is in communication with at least a second multi-contact bio-potential electrode assembly, said communications including measured ECG signals, estimated ECG signals, transfer function, and other useful information.

20. The improvement of claim 16, wherein said electronic patch layer includes a plurality of electrical contacts for attaching a plurality of extended leads for measurement of a plurality of long-lead signals.

21. The improvement of claim 16, wherein said system is employed in conjunction with a standard ECG measurement system to improve performance against failed leads.

22. The improvement of claim 16, wherein said processing unit is disposed in said electronic patch layer of said electrode assembly.

23. The improvement of claim 22, wherein said processing unit is comprised of a digital signal processor.

24. The improvement of claim 16, wherein said system identification technique uses linear state-space model identification.

25. The improvement of claim 16, wherein said transfer function computes estimated long-lead ECG signals based on other estimated long-lead ECG signals and the measured short-lead ECG signals from said plurality of contact points.

26. The improvement of claim 16, wherein said processing unit employs signal processing and analysis on said ECG signals to detect and declare abnormalities.

27. The improvement of claim 16, wherein said electrode assembly is placed in proximity to the cardiac area, including being disposed next to or near the side of the heart.

* * * * *